United States Patent
Watanabe

(10) Patent No.: US 7,842,351 B2
(45) Date of Patent: Nov. 30, 2010

(54) INK COMPOSITION, INKJET RECORDING METHOD, PRINTED MATERIAL, METHOD OF PRODUCING PLANOGRAPHIC PRINTING PLATE, AND PLANOGRAPHIC PRINTING PLATE

(75) Inventor: Kotaro Watanabe, Haibara-gun (JP)

(73) Assignee: Fujifilm Corporation, Tokyo (JP)

( * ) Notice: Subject to any disclaimer, the term of this patent is extended or adjusted under 35 U.S.C. 154(b) by 445 days.

(21) Appl. No.: 11/878,357

(22) Filed: Jul. 24, 2007

(65) Prior Publication Data

US 2008/0173213 A1    Jul. 24, 2008

(30) Foreign Application Priority Data

Jul. 24, 2006   (JP)   ............... 2006-200851

(51) Int. Cl.
| | |
|---|---|
| C09D 11/02 | (2006.01) |
| C07D 303/04 | (2006.01) |
| C08J 7/00 | (2006.01) |
| G03F 7/00 | (2006.01) |
| B05D 1/00 | (2006.01) |
| B41M 5/00 | (2006.01) |

(52) U.S. Cl. ............... 427/466; 430/300; 430/280.1; 522/75; 522/83; 522/168; 522/170

(58) Field of Classification Search ............... 427/510, 427/466; 101/453; 522/168, 75, 83, 170; 430/280.1, 300
See application file for complete search history.

(56) References Cited

U.S. PATENT DOCUMENTS

| | | | | |
|---|---|---|---|---|
| 4,634,548 | A * | 1/1987 | Helmlinger et al. | 426/536 |
| 5,663,030 | A * | 9/1997 | Malhotra | 430/125.6 |
| 6,927,292 | B2 * | 8/2005 | Senn-Bilfinger et al. | 546/64 |
| 7,183,040 | B2 * | 2/2007 | Thies et al. | 430/280.1 |
| 2003/0231234 | A1 | 12/2003 | Ushirogouchi | |
| 2005/0171237 | A1 * | 8/2005 | Patel et al. | 523/160 |
| 2006/0128823 | A1 * | 6/2006 | Tsuchimura et al. | 522/71 |
| 2006/0174799 | A1 * | 8/2006 | Aoai | 106/31.48 |
| 2006/0189716 | A1 * | 8/2006 | Ushirogouchi et al. | 523/160 |
| 2006/0194029 | A1 * | 8/2006 | Tsujihata | 428/195.1 |
| 2006/0222832 | A1 * | 10/2006 | Shimohara | 428/195.1 |
| 2006/0223006 | A1 * | 10/2006 | Shimada et al. | 430/302 |
| 2006/0223823 | A1 * | 10/2006 | Hayashi et al. | 514/253.09 |
| 2008/0008943 | A1 * | 1/2008 | Watanabe | 430/9 |

FOREIGN PATENT DOCUMENTS

| | | | |
|---|---|---|---|
| EP | 0172376 | * | 2/1986 |
| JP | 54-117203 | A | 9/1979 |
| JP | 60-19779 | * | 1/1985 |
| JP | 60-126279 | * | 7/1985 |
| JP | 9-183928 | A | 7/1997 |
| JP | 11-43540 | A | 2/1999 |
| JP | 11-60702 | A | 3/1999 |
| JP | 2003-312121 | A | 11/2003 |
| JP | 2003-341217 | A | 12/2003 |
| JP | 2004-91558 | A | 3/2004 |

OTHER PUBLICATIONS

WO 01/83580 A2, Showa Denko K.K., "Polymerizable Composition, Cured Material Thereof and Method for Manufacturing the Same", PCT Nov. 8, 2001.*
WO 2006/030960 A1, Dainippon Ink and Chemicals, Inc., "Photocationic Curable Composition and New Compound", PCT Mar. 23, 2006.*

* cited by examiner

*Primary Examiner*—Susan W Berman
(74) *Attorney, Agent, or Firm*—Sughrue Mion, PLLC

(57) ABSTRACT

There is provided an ink composition that includes a compound represented by the following formula (I) and that includes a single oxirane fragment, as a partial structure in at least one bicyclic or tricyclic ring, Formula (I)

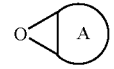

wherein, in the formula (I), A represents a group of atoms forming a bicyclic or tricyclic ring.

15 Claims, No Drawings

INK COMPOSITION, INKJET RECORDING METHOD, PRINTED MATERIAL, METHOD OF PRODUCING PLANOGRAPHIC PRINTING PLATE, AND PLANOGRAPHIC PRINTING PLATE

CROSS-REFERENCE TO RELATED APPLICATION

This application claims priority under 35 USC 119 from Japanese Patent Application No. 2006-200851, the disclosure of which is incorporated by reference herein.

BACKGROUND OF THE INVENTION

1. Field of the Invention

The present invention relates to an ink composition favorably used for inkjet recording, an inkjet recording method, a printed material produced therewith, a planographic printing plate produced using the ink composition, and a method for producing a planographic printing plate.

2. Description of the Related Art

Cyclic ether compounds such as 3-membered rings and 4-membered rings are known to exhibit high reactivity, and are used as polymerizable compounds contained in curable compositions subjected to photocationic polymerization or heat polymerization using an acid anhydride (for example, see Japanese Patent Application Laid-Open (JP-A) Nos. 11-43540 and 11-60702.)

There are many image-recording methods of forming an image on a recording medium such as paper based on image data signals, including those in electrophotographic process, sublimation or fusion heat-transfer process, and inkjet process. Among them, the inkjet process is advantageous in that it allow printing in a cheaper device at a lower running cost, because it forms an image directly on a recording medium by ejecting ink only in desirable image region and thus uses the ink more efficiently. In addition, the inkjet process is also less noisy and thus advantageous as an image-recording method.

The inkjet process allows printing not only on plain paper but also on non-water absorbing recording media such as a plastic sheet or metal plate, but is imperatively required to increase the printing speed and improve the image quality. The time required for drying and curing the ink droplets after printing significantly influences the efficiency in producing printed materials and sharpness of the printed image.

In the inkjet recoding processes, there is a recording method by using an inkjet recording ink that cures by irradiation with radiation ray. In the method, it is possible to improve the printing efficiency and the quality of image, by curing the ink droplet by irradiating it with radiation ray immediately or after a particular period from ejection.

By increasing the sensitivity of the inkjet recording ink which is curable by irradiation with a radiation ray such as ultraviolet light, the ink has higher curability for radiation rays, which brings about many benefits such as the improvement in inkjet recording efficiency, reduction in power consumption, prolongation of the lifetime of radiation ray generator owing to the decrease in the load, and prevention of volatilization of low-molecular substances caused by insufficient curing. Further, the increase in the sensitivity particularly increases the strength of the image formed using the inkjet recording ink. In particular, a planographic printing plate produced using the ink composition has increased strength in the image areas thereof, and thus provides higher printing durability.

In recent year, curable inkjet systems employing a radiation ray such as ultraviolet light is receiving attention because they give relatively less odor, produce fast-drying images, and allow recording on a recording medium which does not absorb ink. A cationic polymerizable ink composition which provides excellent adhesiveness to a recording medium with low shrinkage when exposed to ultraviolet light is supposed (for example, see JP-A No. 9-183928). However, the cationic polymerizable ink is not sufficiently stable during storage because of the reaction caused by the acid generated over time, which is an obstacle to the commercialization of the ink. Therefore, in order to improve the storage stability, a technique of adding a basic compound or a thermal base generator is supposed (for example, see JP-A Nos. 2003-312121, 2003-341217, 2004-91558 and 54-117203). However, there is another problem that the curing sensitivity of the ink deteriorates because the basic compound inhibits the function of the acid generated upon exposure.

However, in recent years, a technique of digitizing image information using a computer by electronically processing, storing, and outputting the information has become widespread, and a new image output system that can be used for the above technique has been desired. In particular, a method for making a printing plate without treatment with a developing solution is studied, and a method for directly making a planographic printing plate using an inkjet recording ink composition is studied (for example, see JP-A No. 54-117203). The method comprises steps of image-wisely ejecting ink on the support surface which is preferably hydrophilic, and curing the ink by irradiation with actinic radiation to make a printing plate having a desired image (preferably a hydrophobic image).

For the formation of image areas on the planographic printing plate, it is desired that, for example, ink droplets ejected on the support immediately cure with no bleeding, the cured image areas have excellent strength and adhesiveness to the support, and the image areas sufficiently conform to the bending of the support and receive no damage such as cracks when the planographic printing plate is mounted on a printing machine. Accordingly, an ink composition suitable to these applications is needed. In particular, a multifunctional cyclic ether, which is used for the purpose of improving the sensitivity of cationic polymerizable ink and cures to form a polymer having a highly crosslinked three-dimensional structure, is desired to be improved for solving the problem of the deterioration in the flexibility of the cured ink coating.

SUMMARY OF THE INVENTION

The present invention has been made in view of the above circumstances and provides. ink composition, inkjet recording method, printed material, method of producing planographic printing plate and planographic printing plate.

A first aspect of the invention provides an ink composition comprising a compound that is represented by the following formula (I) and that contains a single oxirane fragment, as a partial structure in at least one bicyclic or tricyclic ring,

Formula (I)

wherein, in the formula (I), A represents a group of atoms forming a bicyclic or a tricyclic ring.

A second aspect of the invention provides an inkjet recording method including ejecting the ink composition according to the invention onto a recording medium using an inkjet recording apparatus, and curing the ink composition by irradiating the ejected ink composition with actinic radiation.

A third aspect of the invention provides printed material that has been recorded by the inkjet recording method according to the invention.

A forth aspect of the invention provides a method for producing a planographic printing plate, the method including ejecting the ink composition according to the invention onto a support, and forming a hydrophobic image on the support by irradiating the ejected ink composition with actinic radiation to cure the ink composition A fifth aspect of the invention provides a planographic printing plate that has been produced by the method for producing a planographic printing plate according to the invention.

DETAILED DESCRIPTION OF THE INVENTION

The ink composition according to the invention is, in particular, favorably used as an ink composition for inkjet recording, cures highly sensitively by irradiation with a radiation ray such as ultraviolet light, and forms a high quality image.

In the invention, the compound represented by the following formula (I) including a single oxirane fragment as a partial structure in at least fragment as a partial structure in at least one bicyclic or tricyclic ring has a strong van der Waals' force between the side chains thereof, and thus has favorable crystallinity. Such a monofunctional compound added to the ink composition forms an intermolecular crosslinked structure, more specifically, a physical crosslinked structure having excellent mobility than a covalent crosslinked structure. Therefore, when the compound is added to the ink composition with a proper constitution, a high-strength cured film is formed without containing a large amount of polyfunctional polymerizable compound, which is generally used for the purpose of achieving a high-density crosslinked structure, wherein the cured film formed has excellent flexibility owing to the intermolecular crosslinked structure.

Further, by applying the inkjet recording method, the ink composition is cured highly sensitively even when it is ejected on a non-absorbent recording medium, and directly forms high-strength image areas on the basis of digital data. Accordingly, the ink composition according to the invention is favorably used for producing a planographic printing plate, in particular a large planographic printing plate of A2 or larger. The planographic printing plate thus obtained provides excellent printing durability.

According to an aspect of the invention, there is provided an ink composition which cures highly sensitively by irradiation with a radiation ray to form a high-quality image having flexibility, and an inkjet recording method using the ink composition of which the image formed by curing has a flexibility.

Further, according to another aspect of the invention, there is provided a printed material, a planographic printing plate, and a method for making a planographic printing plate using an ink composition which is cured highly sensitively by irradiation with a radiation ray.

<Ink Composition>

The ink composition according to the invention comprises a compound represented by the following formula (I) containing a single oxirane fragment as a partial structure in at least one bicyclic or tricyclic ring (hereinafter, suitably referred to as a specific polymerizable compound).

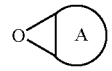

Formula (I)

In the formula, A represents a group of atoms forming a bicyclic or tricyclic ring.

The ink composition according to the invention is a composition which is curable by irradiation with a radiation ray.

The "radiation ray" in the invention is not particularly limited as long as it can provide energy which enables an initiating species to be generated in the composition by the irradiation, and broadly covers α rays, γ rays, X rays, ultraviolet light, visible light, and electron beams. Among them, ultraviolet light and electron beams are preferable from the viewpoint of curing sensitivity and the availability of equipment, and ultraviolet light is particularly preferable. Accordingly, the ink composition according to the invention is preferably an ink composition which is curable by ultraviolet irradiation.

The specific polymerizable compound in the invention is preferably a compound which initiates a polymerization reaction to cure the compound by the action of an acid generated from the below-described compound which generates an acid by irradiation with a radiation ray.

A particularly preferable embodiment of the ink composition according to the invention is an ink composition composed of the specific polymerizable compound. The structure of the ink composition is illustrated below, but it will be understood that the invention is not limited to it.

[Compound Represented by the Following Formula (I) Containing a Single Oxirane Fragment as a Partial Structure in at Least One Bicyclic or Tricyclic Ring]

The specific polymerizable compound according to the invention is further described below.

The ink composition according to the invention comprises a compound represented by the following formula (I) containing a single oxirane fragment as a partial structure in at least one bicyclic or tricyclic ring. More specifically, the following formula (I) indicates that the oxirane and bicyclic or tricyclic ring forms a crosslinked ring in which two carbon atoms of the 3-membered ring forming the oxirane fragment are shared between them.

Further, the compound represented by the following formula (I) has excellent crystallinity. The specific polymerizable compound include compounds which are solid at normal temperature (25° C.).

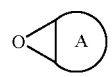

Formula (I)

In the formula, A represents a group of atoms forming a bicyclic or tricyclic ring.

Hereinafter, the at least one bicyclic or tricyclic ring, and a single oxirane fragment are described in detail below.

(A Single Oxirane Fragment)

The specific polymerizable compound in the invention includes a single oxirane fragment. That is to say, the specific polymerizable compound contains a single oxirane fragment. When the compound contains a single oxirane fragment, this is a state in which polymerization sites are reduced to a minimum, which is preferable for improving the flexibility of the cured film.

In the invention, the single oxirane fragment must be directly bonded to the below-described at least one bicyclic or tricyclic ring with two carbon atoms in the 3-membered ring forming the oxirane fragment shared between them, wherein the carbon atoms may have a substituent.

Examples of the substituent, which can be introduced, include an alkyl group, an alkenyl group, an alkynyl group, an aryl group, an aralkyl group, a hydrogen atom, a halogen atom, a hydroxyl group, and a mercapto group. Among them, a methyl group is preferable.

In the invention, the position of the substituent in the oxirane fragment is optional.

(At Least One Bicyclic or Tricyclic Ring)

The specific polymerizable compound in the invention has within the molecule thereof at least one bicyclic or tricyclic ring.

In the invention, a bicyclic ring refers to a ring which requires two disconnections of ring bonds to convert the ring into an open-chain structure, and a tricyclic ring refers to a ring which requires three disconnections. The atoms forming such a ring in the structure are not particularly limited. However, such a ring preferably composed from oxygen and/or carbon atoms, and more preferably composed from carbon atoms. The ring structure preferably is formed from 6 to 18 carbon atoms, and more preferably 7 to 12 carbon atoms.

In the invention, the number of the bicyclic or tricyclic ring contained in one molecule of the specific polymerizable compound is at least one, and preferably one or two.

The at least one bicyclic or tricyclic ring in the invention may have a substituent. Examples of the substituent, which can be introduced, include an alkyl group, an alkenyl group, an alkynyl group, an aryl group, an aralkyl group, a hydrogen atom, a halogen atom, a hydroxyl group, and a mercapto group. Among them, an alkyl group is more preferable, and a methyl group is particularly preferable. The position of the substituent in the at least one bicyclic or tricyclic ring is optional. Typical specific examples (a-1 to a-6) of the specific polymerizable compound in the invention are shown below, however the invention is not limited to these specific examples.

a-1

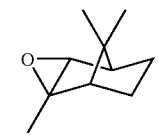
a-2

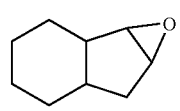
a-3

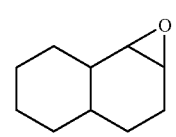
a-4

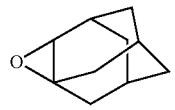
a-5

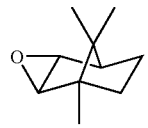
a-6

The specific polymerizable compound in the invention may be synthesized by the method described in Shinjikken kagaku Koza (Sanka to Kangen [I-2])(Maruzen).

In the ink composition according to the invention, the content of the specific polymerizable compound is preferably from 0.5 to 20 mass %, more preferably from 1 to 15 mass %, and further preferably 1.5 to 10 mass % with respect to the total solid content constituting the ink composition according to the invention.

In the invention, the total content of the specific polymerizable compound and monofunctional monomers other than the specific polymerizable compound (total content of polymerizable compounds) is preferably from 40 to 90 mass %, more preferably 45 to 80 mass %, and most preferably 50 to 70 mass % with respect to the total solid content constituting the ink composition according to the invention.

The ink composition according to the invention may comprise, within a range which does not impair the effect of the invention, in addition to the specific polymerizable compound the below-described another polymerizable compound (a cationic polymerizable compound).

In the invention, from the viewpoint of effectively suppressing the shrinkage of the composition during curing, it is preferable that the specific polymerizable compound be used in combination with the below-described another polymerizable compound, more specifically at least one compound selected from epoxy compounds, vinyl ether compounds, and other oxetane compounds not included in the specific polymerizable compound.

(Another Polymerizable Compounds)

Another cationic polymerizable compound used in the invention is not particularly limited, if it is a compound as described below that initiates polymerization reaction and cures by an acid generated from a compound that generates acid by irradiation of a radiation ray, and any one of various cationically polymerizable monomers known as photocationically polymerizable monomers may be used. Examples of the cation polymerizable monomers include epoxy compounds, vinyl ether compounds, and other oxetane compounds not included in the specific polymerizable compounds that are described in JP-A Nos. 6-9714, 2001-31892, 2001-40068, 2001-55507, 2001-310938, 2001-310937, and 2001-220526 and others, and the like.

The epoxy compounds include aromatic epoxides, alicyclic epoxides, aromatic epoxides, and the like.

The aromatic epoxides are, for example, di- or poly-glycidyl ethers prepared in reaction of a polyvalent phenol having at least one aromatic ring or the alkyleneoxide adduct thereof with epichlorohydrin, and example thereof include di- or poly-glycidyl ethers of bisphenol A or the alkyleneoxide adduct thereof, di- or poly-glycidyl ethers of a hydrogenated bisphenol A or the alkyleneoxide adduct thereof, novolak epoxy resins, and the like. The alkyleneoxide is ethyleneoxide, propyleneoxide, or the like.

Preferable examples of the alicyclic epoxides include compounds containing cyclohexene oxide or cyclopentene oxide prepared through epoxidation of a compound having at least one cycloalkane ring such as a cyclohexene or cyclopentene ring with an appropriate oxidant such as hydrogen peroxide or peroxy acid.

Examples of the aliphatic epoxide include diglycidyl or polyglycidyl ethers of aliphatic polyhydric alcohols or alkylene oxide adducts thereof, and typical examples thereof include diglycidyl ethers of alkylene glycols such as diglycidyl ether of ethylene glycol, diglycidyl ether of propylene glycol, and diglycidyl ether of 1,6-hexanediol, polyglycidyl ethers of polyhydric alcohols such as diglycidyl or triglycidyl ether of glycerol or alkylene oxide adducts thereof, diglycidyl ethers of polyalkylene glycols such as diglycidyl ether of polyethylene glycol or alkylene oxide adducts thereof, and diglycidyl ether of polypropylene glycol or alkylene oxide adducts thereof. Examples of the alkylene oxide include ethylene oxide and propylene oxide.

The monofunctional and polyfunctional epoxy compounds for use in the invention will be described in detail below.

Examples of the monofunctional epoxy compounds include phenyl glycidylether, p-tert-butylphenyl glycidylether, butyl glycidylether, 2-ethylhexyl glycidylether, allyl glycidylether, 1,2-butyleneoxide, 1,3-butadienemonooxide, 1,2-epoxydodecane, epichlorohydrin, 1,2-epoxydecane, styreneoxide, cylcohexeneoxide, 3-methacryloyloxymethylcylcohexeneoxide, 3-acryloyloxymethylcylcohexeneoxide, 3-vinylcylcohexeneoxide, and the like.

Examples of the multifunctional epoxy compounds include bisphenol A diglycidylether, bisphenol F diglycidylether, bisphenol S diglycidylether, brominated bisphenol A diglycidylether, brominated bisphenol F diglycidylethers, brominated bisphenol S diglycidylether, epoxy novolak resins, hydrogenated bisphenol A diglycidylethers, hydrogenated bisphenol F diglycidylethers, hydrogenated bisphenol S diglycidylethers, 3,4-epoxycyclohexylmethyl-3',4'-epoxycyclohexanecarboxylate, 2-(3,4-epoxycyclohexyl-5,5-spiro-3,4-epoxy)cyclohexane-meta-dioxane, bis(3,4-epoxycyclohexylmethyl) adipate, vinylcylcohexeneoxide, 4-vinylepoxycyclohexane, bis(3,4-epoxy-6-methylcyclohexylmethyl) adipate, 3,4-epoxy-6-methylcyclohexyl-3',4'-epoxy-6'-methylcyclohexanecarboxylate, methylene-bis(3,4-epoxycyclohexane), dicyclopentadiene diepoxide, ethylene glycol di(3,4-epoxycyclohexylmethyl)ether, ethylene bis(3,4-epoxycyclohexanecarboxylate), epoxyhexahydrodioctyl phthalate, epoxyhexahydrodi-2-ethylhexyl phthalate, 1,4-butanediol diglycidylether, 1,6-hexanediol diglycidylether, glycerol triglycidylether, trimethylolpropane triglycidylether, polyethylene glycol diglycidylether, polypropylene glycol diglycidylether, 1,1,3-tetradecadienedioxide, limonenedioxide, 1,2,7,8-diepoxyoctane, 1,2,5,6-diepoxycyclooctane, and the like.

Among these epoxy compounds, aromatic and alicyclic epoxides are preferable from the viewpoint of curing speed, and alicyclic epoxides are particularly preferable.

Examples of the vinyl ether compounds include di- or tri-vinyl ether compounds such as ethylene glycol divinylether, diethylene glycol divinylether, triethylene glycol divinylether, propylene glycol divinylether, dipropylene glycol divinylether, butanediol divinylether, hexanediol divinylether, cyclohexanedimethanol divinylether, and trimethylolpropane trivinylether; monovinylether compounds such as ethyl vinylether, n-butyl vinylether, isobutyl vinylether, octadecyl vinylether, cyclohexyl vinylether, hydroxybutyl vinylether, 2-ethylhexyl vinylether, cyclohexanedimethanol monovinylether, n-propyl vinylether, isopropyl vinylether, isopropenylether-O-propylene carbonate, dodecyl vinylether, diethylene glycol monovinylether, and octadecyl vinylether; and the like.

Hereinafter, the monofunctional and multifunctional vinyl ethers will be described in detail.

Examples of the monofunctional vinylethers include methyl vinylether, ethyl vinylether, propyl vinylether, n-butyl vinylether, t-butyl vinylether, 2-ethylhexyl vinylether, n-nonyl vinylether, lauryl vinylether, cyclohexyl vinylether, cyclohexylmethyl vinylether, 4-methylcyclohexylmethyl vinylether, benzyl vinylether, dicyclopentenyl vinylether, 2-dicyclopentenoxyethyl vinylether, methoxyethyl vinylether, ethoxyethyl vinylether, butoxyethyl vinylether, methoxyethoxyethyl vinylether, ethoxyethoxyethyl vinylether, methoxypolyethylene glycol vinylether, tetrahydrofurfuryl vinylether, 2-hydroxyethyl vinylether, 2-hydroxypropyl vinylether, 4-hydroxybutyl vinylether, 4-hydroxymethylcyclohexylmethyl vinylether, diethylene glycol monovinylether, polyethylene glycol vinylether, chloroethyl vinylether, chlorobutyl vinylether, chloroethoxyethyl vinylether, phenylethyl vinylether, phenoxypolyethylene glycol vinylether, and the like.

Examples of the multifunctional vinylethers include divinyl ethers such as ethylene glycol divinylether, diethylene glycol divinylether, polyethylene glycol divinylether, propylene glycol divinylether, butylene glycol divinylether, hexanediol divinylether, bisphenol A alkyleneoxide divinylethers, and bisphenol F alkyleneoxide divinylethers; multifunctional vinyl ethers such as trimethylolethane trivinylether, trimethylolpropane trivinylether, ditrimethyrollpropane tetravinylether, glycerol trivinylether, pentaerythritol tetravinylether, dipentaerythritol pentavinylether, dipentaerythritol hexavinylether, ethyleneoxide adducts of trimethylolpropane trivinylether, propyleneoxide adducts of trimethylolpropane trivinylether, ethyleneoxide adducts of ditrimethyrollpropane tetravinylether, propyleneoxide adducts of ditrimethyrollpropane tetravinylether, ethyleneoxide adducts of pentaerythritol tetravinylether, propyleneoxide adducts of pentaerythritol tetravinylether, ethyleneoxide adducts of dipentaerythritol hexavinylether, and propyleneoxide adducts of dipentaerythritol hexavinylether, and the like.

Examples of the multifunctional vinylethers include divinyl ethers such as ethylene glycol divinylether, diethylene glycol divinylether, polyethylene glycol divinylether, propylene glycol divinylether, butylene glycol divinylether, hexanediol divinylether, bisphenol A alkyleneoxide divinylethers, and bisphenol F alkyleneoxide divinylethers; multifunctional vinyl ethers such as trimethylolethane trivinylether, trimethylolpropane trivinylether, ditrimethyrollpropane tetravinylether, glycerol trivinylether, pentaerythritol tetravinylether, dipentaerythritol pentavinylether, dipentaerythritol hexavinylether, ethyleneoxide adducts of trimethylolpropane trivinylether, propyleneoxide adducts of trimethylolpropane trivinylether, ethyleneoxide adducts of ditrimethyrollpropane tetravinylether, propyleneoxide adducts of ditrimethyrollpropane tetravinylether, ethyleneoxide adducts of pentaerythritol tetravinylether, propyleneoxide adducts of pentaerythritol tetravinylether, ethyleneoxide adducts of dipentaerythritol hexavinylether, and propyleneoxide adducts of dipentaerythritol hexavinylether, and the like.

Di- or tri-vinylether compounds are preferable as the vinyl ether compounds, form the viewpoints of curing efficiency, adhesiveness to recording medium, and the surface hardness of formed image; and divinylether compounds are particularly preferable.

The other oxetane compounds which may be additionally used in the invention may be freely selected from known oxetane compounds such as those described in JP-A Nos. 2001-220526, 2001-310937, and 2003-341217. In the invention, the compound having an oxetane ring which may be used in combination with the specific polymerizable compound is preferably a compound having 1 to 4 oxetane rings in the structure thereof. The use of the compound facilitates maintenance of the viscosity of the composition within a range which achieves favorable processability, and, in cases where the composition is used as an ink composition, ensures high adhesiveness between the cured composition and a recording medium.

Examples of the compounds having one or two oxetane rings in the molecule that are used additionally in the invention include the compounds represented by the following formulae (1) to (3), and the like.

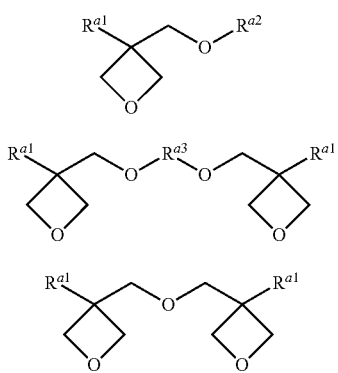

$R^{a1}$ represents a hydrogen atom, an alkyl group having 1 to 6 carbon atoms, a fluoroalkyl group having 1 to 6 carbon atoms, an allyl group, an aryl group, a furyl group, or a thienyl group. In cases where two $R^{a1}$ s are present in the molecule, they may be the same or different from each other.

Examples of the alkyl group include a methyl group, an ethyl group, a propyl group, and a butyl group, and any of hydrogen atoms in these alkyl groups may be substituted with a fluorine atom, which are preferable as the fluoroalkyl group.

$R^{a2}$ represents a hydrogen atom, an alkyl group having 1 to 6 carbon atoms, an alkenyl group having 2 to 6 carbon atoms, an aromatic ring-containing group, an alkylcarbonyl group having 2 to 6 carbon atoms, an alkoxycarbonyl group having 2 to 6 carbon atoms, and an N-alkylcarbamoyl group having 2 to 6 carbon atoms. Examples of the alkyl group include a methyl group, an ethyl group, a propyl group, and a butyl group. Examples of the alkenyl group include a 1-propenyl group, a 2-propenyl group, a 2-methyl-1-propenyl group, a 2-methyl-2-propenyl group, a 1-butenyl group, a 2-butenyl group, and a 3-butenyl group. Examples of the aromatic ring-containing group include a phenyl group, a benzyl group, a fluorobenzyl group, a methoxybenzyl group, and a phenoxyethyl group. Examples of the alkylcarbonyl group include an ethylcarbonyl group, a propylcarbonyl group, and a butylcarbonyl group. Examples of the alkoxycarbonyl group include an ethoxycarbonyl group, a propoxycarbonyl group, and a butoxycarbonyl group. Examples of the N-alkylcarbamoyl group include an ethylcarbamoyl group, a propylcarbamoyl group, a butylcarbamoyl group, and a pentylcarbamoyl group. $R^{a2}$ may be optionally substituted, and examples of the substituent include an alkyl group having 1 to 6 carbon atoms, and a fluorine atom.

$R^{a3}$ represents a linear or branched alkylene group, a linear, a linear or branched unsaturated hydrocarbon group, a carbonyl group or a carbonyl group-containing alkylene group, a carboxyl group-containing alkylene group, a carbamoyl group-containing alkylene group, or a group shown below. Examples of the alkylene groups include ethylene, propylene, and butylene groups and the like; and examples of the poly (alkyleneoxy) groups include poly(ethyleneoxy) and poly (propyleneoxy) groups and the like. Examples of the unsaturated hydrocarbon groups include propenylene, methylpropenylene, and butenylene groups, and the like.

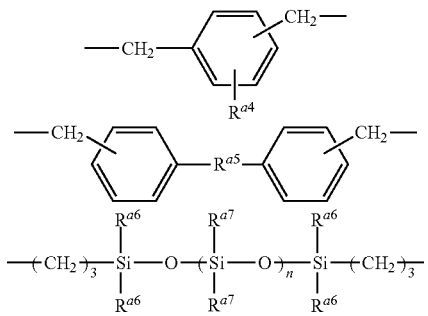

In cases where $R^{a3}$ is one of the above-described polyvalent groups, $R^{a4}$ represents a hydrogen atom, an alkyl group having 1 to 4 carbon atoms, an alkoxy group having 1 to 4 carbon atoms, a halogen atom, a nitro group, a cyano group, a mercapto group, a lower alkyl carboxyl group, a carboxyl group, or a carbamoyl group. $R^{a5}$ represents an oxygen atom, a sulfur atom, a methylene group, NH, SO, $SO_2$, $C(CF_3)_2$, or $C(CH_3)_2$. $R^{a6}$ represents an alkyl group having 1 to 4 carbon atoms, or an aryl group, and n is an integral number of 0 to 2,000. $R^{a7}$ represents an alkyl group having 1 to 4 carbon atoms, an aryl group, or a monovalent group having the structure shown below. In the following formula, $R^{a8}$ represents an alkyl group having 1 to 4 carbon atoms or an aryl group, and m is an integral number of 0 to 100.

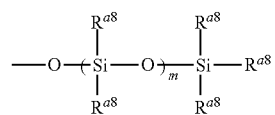

Examples of the compounds represented by the formula (1) include 3-ethyl-3-hydroxymethyloxetane (OXT-101: manufactured by Toagosei Co., Ltd.), 3-ethyl-3-(2-ethylhexyloxymethyl)oxetane (OXT-212: manufactured by Toagosei Co., Ltd.), and 3-ethyl-3-phenoxymethyloxetane (OXT-211: manufactured by Toagosei Co., Ltd.). Examples of the compounds represented by the formula (2) include 1,4-bis[(3-ethyl-3-oxetanylmethoxy)methyl]benzene (OXT-121: Toagosei Co., Ltd. In addition, examples of the compounds represented by the formula (3) include bis(3-ethyl-3-oxetanylmethyl)ether (OXT-221: Toagosei Co., Ltd.).

Examples of the compounds having 3 or 4 oxetane rings include the compounds represented by the following formula (4).

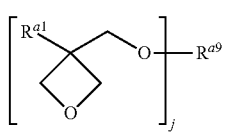

(4)

In formula (4), $R^{a1}$ is the same as that in formula (1) above. Examples of the polyvalent connecting group $R^{a9}$ include branched alkylene group having 1 to 12 carbon atoms such as the groups represented by the following groups A to C, branched poly(alkyleneoxy) groups such as the groups represented by the following group D, and branched polysiloxy groups such as the group represented by the following group E, and the like. j is 3 or 4.

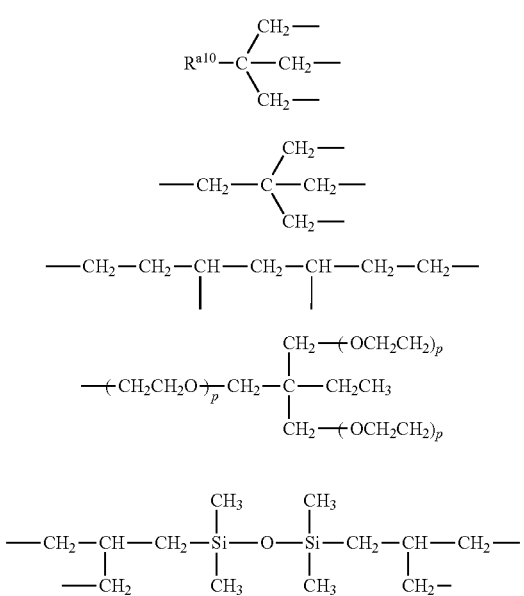

In the group A, $R^{a10}$ represents a methyl, ethyl or propyl group. In the group D, p is an integer of 1 to 10.

Other examples of the oxetane compounds favorably used in the invention include compounds represented by the following formula (5) having oxetane rings on the side chains.

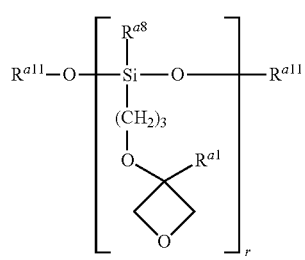

(5)

In formula (5), $R^{a1}$ and $R^{a8}$ are the same as that in the above formula. $R^{a11}$ represents an alkyl group having 1 to 4 carbon atoms or a trialkylsilyl group such as a methyl group, an ethyl group, a propyl group, or a butyl group, and r is an integral number of 1 to 4.

The compounds having an oxetane ring are described in detail in JP-A No. 2003-341217, paragraphs [0021] to [0084], and these compounds are favorably used in the invention.

The oxetane compound described in JP-A No. 2004-91556 may be used in combination in the invention. The compound is described in detail in JP-A No. 2004-91556, paragraphs [0022] to [0058].

Among the other oxetane compounds which may be used in the invention, compounds having one oxetane ring is preferable from the viewpoint of the viscosity and tackiness of the composition.

In the invention, in cases where the specific polymerizable compound is used in combination with other cationic polymerizable compound, the content ratio between the specific polymerizable compound and the other cationic polymerizable compound is preferably 10:1 to 10:100, more preferably 10:3 to 10:80, and further preferably 10:5 to 10:60 in terms of mass ratio.

[Compound Generating an Acid by Irradiation with a Radiation Ray]

The ink composition according to the invention preferably contains a compound which generates an acid by irradiation with a radiation ray (hereinafter, also referred to as "photo acid generator"). In the invention, the acid generated by irradiation with a radiation ray induces the above-described polymerizable compound to polymerize to cure.

The photo acid generating agent may be selected properly from photo initiators for photocationic polymerization, photo initiators for photoradical polymerization, photo-erasing agent for dyes, photo discoloring agents, and compounds generating an acid by irradiation with light used for microresist or the like (for example, ultraviolet light of 400 to 200 nm, far ultraviolet light, most preferably g rays, h rays, i rays, or KrF excimer laser light), ArF excimer laser light, electron beams, X rays, molecular beams, or ion beams.

Examples of the photo acid generating agents include onium salt compounds such as diazonium salts, phosphonium salts, sulfonium salts and iodonium salts and sulfonate compounds such as imidosulfonates, oxime sulfonates, diazodisulfones, disulfones, and o-nitrobenzyl sulfonates that decompose and generate acid by irradiation with radiation ray, and the like.

Examples of the other compounds (photo acid generating agents) which generates an acid by irradiation with activated light or a radiation ray used in the invention include: diazonium salts described in S. I. Schlesinger, Photogr. Sci. Eng., 18, 387 (1974), T. S. Bal et al, Polymer, 21, 423 (1980), and others; ammonium salts described in U.S. Pat. Nos. 4,069,055, 4,069,056, and Re27,992, JP-A No. 3-140140, and others; phosphonium salts described in D. C. Necker et al, Macromolecules, 17, 2468 (1984), C. S. Wen et al, Teh, Proc. Conf. Rad. Curing ASIA, p478, Tokyo, October (1988), U.S. Pat. Nos. 4,069,055 and 4,069,056, and others; iodonium salts described in J. V. Crivello et al, Macromorecules, 10 (6), 1307 (1977), Chem. & Eng. News, Nov. 28, p. 31 (1988), European Patent Application Nos. 104,143, 339,049, and 410,201, JP-A Nos. 2-150848 and 2-296514, and others; sulfonium salts described in J. V. Crivello et al, Polymer J. 17, 73 (1985), J. V. Crivello et al. J. Org. Chem., 43, 3055 (1978), W. R. Watt et al, J. Polymer Sci, Polymer Chem. Ed., 22, 1789 (1984), J. V. Crivello et al, Polymer Bull., 14, 279 (1985), J. V. Crivello et al, Macromorecules, 14 (5), 1141 (1981), J. V. Crivello et al, J. Polymer Sci., Polymer Chem. Ed., 17, 2877

(1979), European Patent Application Nos. 370,693, 161,811, 410,201, 339,049, 233,567, 297,443, and 297,442, U.S. Pat. Nos. 3,902,114, 4,933,377, 4,760,013, 4,734,444, and 2,833,827, German Patent Nos. 2904,626, 3,604,580, and 3,604,581, JP-A Nos. 7-28237, and 8-27102, and others; selenonium salts described in J. V. Crivello et al, Macromorecules, 10 (6), 1307 (1977), J. V. Crivello et al, J. Polymer Sci., Polymer Chem. Ed., 17, 1047 (1979), and others; onium salts such as arsonium salts described in C. S. Wen et al, Teh, Proc. Conf. Rad. Curing ASIA, p478, Tokyo, October (1988); organic halogen compounds described in U.S. Pat. No. 3,905,815, Japanese Patent Application Publication (JP-B) No. 46-4605, JP-A Nos. 48-36281, 55-32070, 60-239736, 61-169835, 61-169837, 62-58241, 62-212401, 63-70243, and 63-298339, and others; organic metals/organic halides described in K. Meier et al, J. Rad. Curing, 13 (4), 26 (1986), T. P. Gill et al, Inorg. Chem., 19, 3007 (1980), D. Astruc, Acc. Chem. Res., 19 (12), 377 (1986), JP-A No. 2-161445, and others;

photo acid generating agents having an o-nitrobenzyl type protecting group described in S. Hayase et al, J. Polymer Sci., 25, 753 (1987), E. Reichmanis et al, J. Polymer Sci., Polymer Chem. Ed., 23, 1 (1985), Q. Q. Zhu et al, J. Photochem., 36, 85, 39, 317 (1987), B. Amit et al, Tetrahedron Lett., (24) 2205 (1973), D. H. R. Barton et al, J. Chem. Soc., 3571 (1965), P. M. Collins et al, J. Chem. Soc., Perkin I, 1695 (1975), M. Rudinstein et al, Tetrahedron Lett., (17), 1445 (1975), J. W. Walker et al, J. Am. Chem. Soc., 110, 7170 (1988), S. C. Busman et al, J. Imaging Technol., 11 (4), 191 (1985), H. M. Houlihan et al, Macormolecules, 21, 2001 (1988), P. M. Collins et al, J. Chem. Soc., Chem. Commun., 532 (1972), S. Hayase et al, Macromolecules, 18, 1799 (1985), E. Reichmanis et al, J. Electrochem. Soc., Solid State Sci. Technokl., 130 (6), F. M. Houlihan et al, Macromolcules, 21, 2001 (1988), European Patent Application Nos. 0290,750, 046,083, 156, 535, 271,851, and 0,388,343, U.S. Pat. Nos. 3,901,710 and 4,181,531, JP-A Nos. 60-198538 and 53-133022, and others;

the sulfone compounds that photodecompose and generate acid such as iminosulfonates described in M. TUNOOKA et al., Polymer Preprints Japan, 35 (8), G. Berner et al., J. Rad. Curing, 13 (4), W. J. Mijs et al., Coating Technol., 55 (697), 45 (1983), Akzo, H. Adachi et al., Polymer Preprints Japan, 37(3), EP Nos. 0199,672, 84515, 044,115, 618,564, and 0101,122, U.S. Pat. Nos. 4,371,605 and 4,431,774, JP-A Nos. 64-18143, 2-245756, and 3-140109, and others; the disulfonated compounds described in JP-A Nos. 61-166544 and 2-71270, and others; and the diazoketosulfone and diazodisulfone compounds described in JP-A Nos. 3-103854, 3-103856, and 4-210960 and others.

In addition, compounds having a group generating acid by the light described above or polymers having such a compound in the main chain or on the side, including those described in M. E. Woodhouse et al., J. Am. Chem. Soc., 104, 5586 (1982), S. P. Pappas et al., J. Imaging Sci., 30 (5), 218 (1986), S. Kondo et al., Macromol. Chem., Rapid Commun., 9, 625 (1988), Y. Yamada et al., Makromol. Chem., 152, 153, 163 (1972), J. V. Crivello et al., J. Polymer Sci., Polymer Chem. Ed., 17, 3845 (1979), U.S. Pat. No. 3,849,137, German Patent No. 3,914,407, JP-A Nos. 63-26653,55-164824, 62-69263, 63-146038, 63-163452, 62-153853, and 63-146029, and others, may also be used. Examples thereof include onium salts such as diazonium salts, ammonium salts, phosphonium salts, iodonium salts, sulfonium salts, selenonium salts, and arsonium salts; organic halogen compounds, organic metals/organic halides, o-nitrobenzyl protecting group-containing photo acid generating agents, sulfone compounds that generates acid by photochemical decomposition such as iminosulfonates, disulfonated compounds, diazoketosulfones, and diazodisulfone compounds.

Other examples include compounds generating an acid by light described in V. N. R. Pillai, Synthesis, (1), 1 (1980), A. Abad et al, Tetrahedron Lett., (47) 4555 (1971), D. H. R. Barton et al, J. Chem. Soc., (C), 329 (1970), U.S. Pat. No. 3,779,778, and European Patent Application No. 126,712 and the like.

Favorable examples of the photo acid generating agents for use in the invention include the compounds represented by the following formulae (b1), (b2), and (b3).

(b1)

(b2)

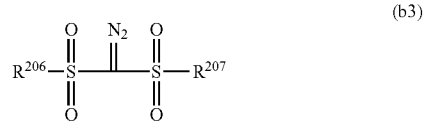

(b3)

In formula (b1), $R^{201}$, $R^{202}$, and $R^{203}$ each independently represent an organic group.

$X^-$ represents a non-nucleophilic anion, and is preferably a sulfonate anion, carboxylate anion, bis(alkylsulfonyl)amide anion, tris(alkylsulfonyl)methide anion, $BF_4^-$, $PF_6^-$, $SbF_6^-$, or a group shown below, and is preferably an organic anion having carbon atoms.

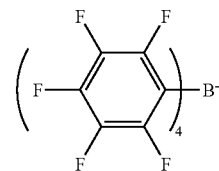

Preferable examples of the organic anion include the following organic anions.

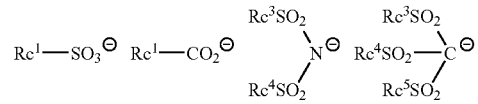

$R^{c1}$ represents an organic group. Examples of the organic group represented by $R^{c1}$ include those having 1 to 30 carbon atoms, and preferable examples thereof include an alkyl group, a cycloalkyl group, an aryl group, and combinations thereof linked through a single bond or a linking group such as —O—, —CO$_2$—, —S—, —SO$_3$—, or —SO$_2$N(Rd$^1$)—.

Rd$^1$ represents a hydrogen atom or an alkyl group. $R^{c3}$, $R^{c4}$, and $R^{c5}$ each independently represent an organic group.

The organic group of $R^{c3}$, $R^{c4}$, or $R^{c5}$ is preferably the same as the organic group favorable as $Rc^1$ and particularly preferably a perfluoroalkyl group having 1 to 4 carbon atoms.

Each of the organic groups represented by $R^{c1}$, and $R^{c3}$ to $R^{c5}$ is most preferably an alkyl group substituted with a fluorine atom or fluoroalkyl group at the 1 position, or a phenyl group substituted with a fluorine atom or a fluoroalkyl group. Through the fluorine atom or fluoroalkyl group increases the acidity of the acid generated by photoirradiation, thereby improving the sensitivity. The organic groups of $R^{201}$, $R^{202}$, and $R^{203}$ usually have 1 to 30 carbon atoms, and preferably 1 to 20 carbon atoms.

Two of $R^{201}$ to $R^{203}$ may be linked together to form a ring structure, and the ring may contain an oxygen atom, a sulfur atom, an ester bond, an amide bond, or a carbonyl group. Examples of the group formed by linkage between two of $R^{201}$ to $R^{203}$ include an alkylene group (for example, a butylene group, and a pentylene group). Specific examples of the organic groups of $R^{201}$, $R^{202}$, and $R^{203}$ include the corresponding groups in the below-described compounds (b1-1), (b1-2), and (b1-3).

The compound may contain a plurality of the structure represented by formula (b1). For example, at least one of $R^{201}$ to $R^{203}$ of the compound represented by formula (b1) may be bonded to at least one of $R^{201}$ to $R^{203}$ of another compound represented by formula (b1) directly or through a linking group.

Preferable examples of the (b1) component include the compounds (b1-1), (b1-2), and (b1-3) described below.

The compound (b1-1) is an arylsulfonium compound in which at least one of $R^{201}$ to $R^{203}$ of formula (b1) is an aryl group, that is, a compound in which the cation thereof is an aryl sulfonium.

In the arylsulfonium compound, all of $R^{201}$ to $R^{203}$ may be an aryl group, or a part of $R^{201}$ to $R^{203}$ may be an aryl group, with the remainder being an alkyl group or a cycloalkyl group.

Examples of the arylsulfonium compounds include triarylsulfonium compounds, diarylalkylsulfonium compounds, aryldialkylsulfonium compounds, diarylcycloalkylsulfonium compounds, aryldicycloalkylsulfonium compounds, and the like.

The aryl group in the arylsulfonium compounds is preferably an aryl group such as phenyl or naphthyl, or a heteroaryl group such as indole or pyrrole, and more preferably a phenyl or indole residue. When the arylsulfonium compound has two or more aryl groups, the two or more aryl groups may be the same as or different from each other.

The alkyl group that the arylsulfonium compound may have as needed is preferably a linear or branched alkyl group having 1 to 15 carbons, and examples thereof include methyl, ethyl, propyl, n-butyl, sec-butyl, and t-butyl groups and the like.

The cycloalkyl group that the arylsulfonium compound may have as needed is preferably a cycloalkyl group having 3 to 15 carbons, and examples thereof include cyclopropyl, cyclobutyl, and cyclohexyl groups, and the like.

The aryl group, alkyl group, and cycloalkyl group of $R^{201}$ to $R^{203}$ may each have an alkyl group (for example, one having 1 to 15 carbon atoms), a cycloalkyl group (for example, one having 3 to 15 carbon atoms), an aryl group (for example, one having 6 to 14 carbon atoms), an alkoxy group (for example, one having 1 to 15 carbon atoms), a halogen atom, a hydroxyl group, or a phenylthio group as a substituent. As the substituent, a linear or branched alkyl group having 1 to 12 carbon atoms, a cycloalkyl group having 3 to 12 carbon atoms, and a linear, branched, or cyclic alkoxy group having 1 to 12 carbon atoms are preferable, and an alkyl group having 1 to 4 carbon atoms, and an alkoxy group having 1 to 4 carbon atoms are most preferable. The substituent may replace any one of $R^{201}$ to $R^{203}$, or all of $R^{201}$ to $R^{203}$. Also, in cases where $R^{201}$ to $R^{203}$ are an aryl group, it is preferable that the substituent replace the p-position of the aryl group.

Hereinafter, the compound (b1-2) will be described.

The compound (b1-2) is a compound represented by the formula (b1), wherein $R^{201}$ to $R^{203}$ each independently represent a non-aromatic ring-containing organic group. The aromatic rings include aromatic rings containing a heteroatom.

The non-aromatic ring-containing organic group of $R^{201}$ to $R^{203}$ generally has 1 to 30 carbon atoms and preferably 1 to 20 carbon atoms.

$R^{201}$ to $R^{203}$ each independently, preferably represent an alkyl, cycloalkyl, allyl, or vinyl group, more preferably a linear, branched, or cyclic 2-oxoalkyl group or an alkoxycarbonylmethyl group, and particularly preferably a linear or branched 2-oxoalkyl group.

The alkyl group of $R^{201}$ to $R^{203}$ may be linear or branched, and is preferably a linear or branched alkyl group having 1 to 10 carbon atoms (for example, a methyl group, an ethyl group, a propyl group, a butyl group, and a pentyl group), and more preferably a linear or branched 2-oxoalkyl group, or a linear or branched alkoxycarbonylmethyl group.

The cycloalkyl group of $R^{201}$ to $R^{203}$ is preferably a cycloalkyl group having 3 to 10 carbon atoms (for example, a cyclopentyl group, a cyclohexyl group, and a norbornyl group), and more preferably a cyclic 2-oxoalkyl group.

The linear, branched, or cyclic 2-oxoalkyl group of $R^{201}$ to $R^{203}$ is preferably a group having >C=O at the 2-position of the above-described alkyl group or cycloalkyl group. The alkoxy group in the alkoxycarbonylmethyl group of $R^{201}$ to $R^{203}$ is preferably an alkoxy group having 1 to 5 carbon atoms (for example, a methoxy group, an ethoxy group, a propoxy group, a butoxy group, and a pentoxy group).

$R^{201}$ to $R^{203}$ may be further substituted with a halogen atom, an alkoxy group (for example, one having 1 to 5 carbon atoms), a hydroxy group, a cyano group, or a nitro group.

The compound (b1-3) is a compound represented by the following formula (b1-3), i.e., a compound having a phenacyl sulfonium salt structure.

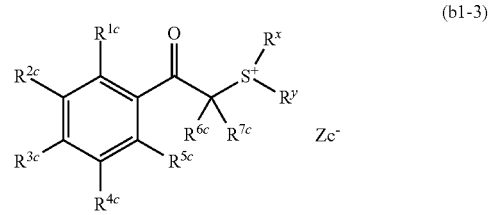

(b1-3)

In formula (b1-3), $R^{1c}$ to $R^{5c}$ each independently represent a hydrogen atom, an alkyl group, a cycloalkyl group, an alkoxy group, or a halogen atom. $R^{6c}$ and $R^{7c}$ each independently represent a hydrogen atom, an alkyl group, or a cycloalkyl group. $R^x$ and $R^y$ each independently represent an alkyl group, a cycloalkyl group, an allyl group, or a vinyl group.

Any two or more of $R^{1c}$ to $R^{5c}$, $R^{6c}$ and $R^{7c}$, and $R^x$ and $R^y$ may be respectively linked together to form a ring structure.

$Zc^-$ represents a non-nucleophilic anion, and may be the same as the non-nucleophilic anion of $X^-$ in formula (b1).

The alkyl group of $R^{1c}$ to $R^{7c}$ may be a straight-chain or branching group, and examples thereof include linear or branched alkyl groups having 1 to 20 carbon atoms, preferably having 1 to 12 carbon atoms, (e.g., methyl, ethyl, linear or branched propyl, linear or branched butyl, and linear or branched pentyl).

The cycloalkyl group of $R^{1c}$ to $R^{7c}$ is preferably a cycloalkyl having 3 to 8 carbon atoms (for example, a cyclopentyl group, and a cyclohexyl group). The alkoxy group of $R^{1c}$ to $R^{5c}$ may be a straight-chain, branched, or cyclic group, and examples thereof include alkoxy groups having 1 to 10 carbons, preferably, straight-chain and branched alkoxy groups having 1 to 5 carbons (e.g., methoxy, ethoxy, straight-chain or branched propoxy, straight-chain or branched butoxy, and straight-chain or branched pentoxy groups), and cyclic alkoxy groups having 3 to 8 carbons (e.g., cyclopentyloxy and cyclohexyloxy groups).

Examples of the groups formed by binding of any two or more of $R^{1c}$ to $R^{5c}$, $R^{6c}$ and $^{7c}$, or $R^{x}$ and $R^{y}$ include butylene and pentylene groups and the like. The ring structure may contain an oxygen or sulfur atom or an ester or amide bond.

Preferably, part of the $R^{1c}$ to $R^{5c}$ are linear or branched alkyl groups, cycloalkyl groups, or linear, branched, or cyclic alkoxy groups; and more preferably, the total number of carbons in groups $R^{1c}$ to $R^{5c}$ is 2 to 15. Under such a condition, the acid generator is more soluble in solvent, suppressing generation of particles during storage.

The alkyl group or cycloalkyl group of $R^x$ and $R^y$ may be the same as the alkyl group or cycloalkyl group of $R^{1c}$ to $R^{7c}$.

$R^x$ and $R^y$ are preferably a 2-oxoalkyl group or an alkoxycarbonylmethyl group.

The 2-oxoalkyl group may be a group having >C=O at the 2-position of the alkyl group or cycloalkyl group of $R^{1c}$ to $R^{5c}$.

The alkoxy group in the alkoxycarbonylmethyl group may be the same as the alkoxy group of $R^{1c}$ to $R^{5c}$.

$R^x$ and $R^y$ are each preferably an alkyl group or cycloalkyl group having 4 or more carbon atoms, and more preferably an alkyl group or cycloalkyl group having 6 or more carbon atoms, and further preferably an alkyl group or cycloalkyl group having 8 or more carbon atoms.

In formulae (b2) and (b3), $R^{204}$ to $R^{207}$ each independently represent an aryl group, an alkyl group, or a cycloalkyl group. $X^-$ represents a non-nucleophilic anion, and may be the same as the non-nucleophilic anion as $X^-$ in formula (b1).

The aryl group of $R^{204}$ to $R^{207}$ is preferably a phenyl or naphthyl group and more preferably a phenyl group.

The alkyl group of $R^{204}$ to $R^{207}$ may be a linear or branched group, and is preferably, for example, a linear or branched alkyl group having 1 to 10 carbons (e.g., methyl, ethyl, propyl, butyl, or pentyl). The cycloalkyl group of $R^{204}$ to $R^{207}$ is preferably, for example, a cycloalkyl group having 3 to 10 carbons (e.g., cyclopentyl, cyclohexyl, or norbornyl).

Examples of the substituent groups that $R^{204}$ to $R^{207}$ may have include alkyl groups (e.g., those having 1 to 15 carbon atoms), cycloalkyl groups (e.g., those having 3 to 15 carbon atoms), aryl groups (e.g., those having 6 to 15 carbon atoms), alkoxy groups (e.g., those having 1 to 15 carbon atoms), halogen atoms, a hydroxyl group, a phenylthio group, and the like.

Other usable examples of the compounds that generates acid by irradiation of activated light or radiation ray include the compounds represented by the following formulae (b4), (b5), and (b6).

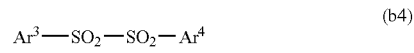
(b4)

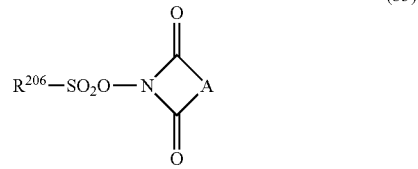
(b5)

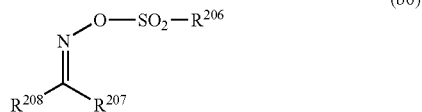
(b6)

In formulae (b4) to (b6), $Ar^3$ and $Ar^4$ each independently represent an aryl group.

$R^{206}$, $R^{207}$ and $R^{208}$ each independently represent an alkyl, cycloalkyl or aryl group.

A represents an alkylene, alkenylene or arylene group.

Among the photo acid generating agents above, preferable are the compounds represented by the formulae (b1) to (b3) and the like.

Favorable examples of the photo acid generating agents for use in the invention (b), (b-1) to (b-96), will be listed below, but the invention is not restricted by these examples.

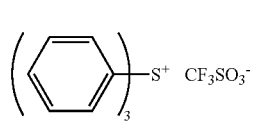
(b-1)

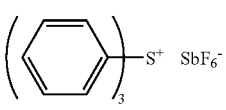
(b-2)

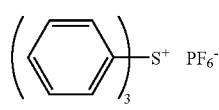
(b-3)

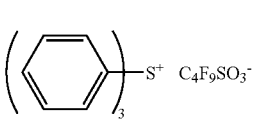
(b-4)

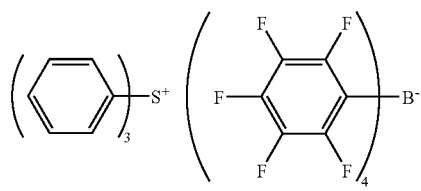
(b-5)

(b-6)

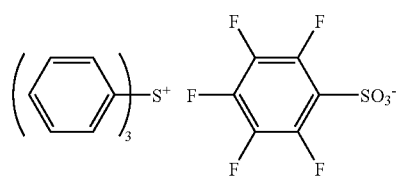
(b-7)
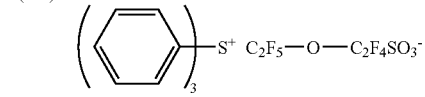
(b-8)
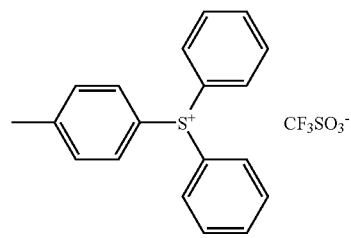
(b-9)
(b-10)
(b-11)
(b-12)
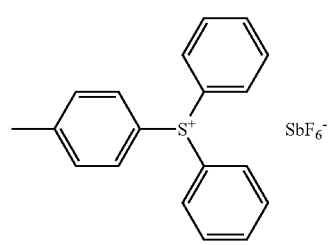
(b-13)
(b-14)
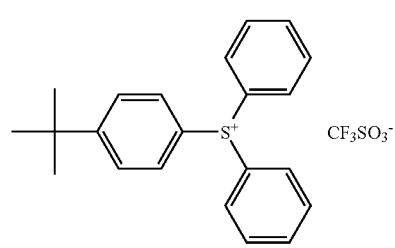
(b-15)
(b-16)
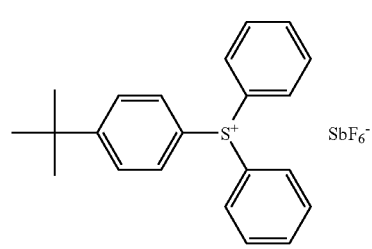
(b-17)
(b-18)
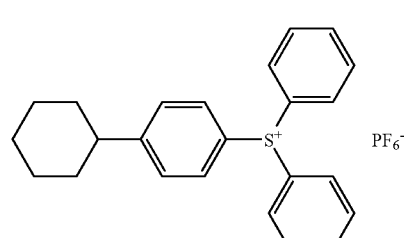
(b-19)
(b-20)
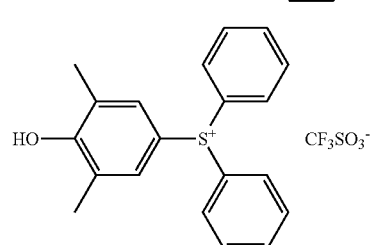
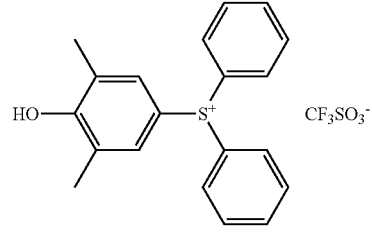

-continued
(b-21)
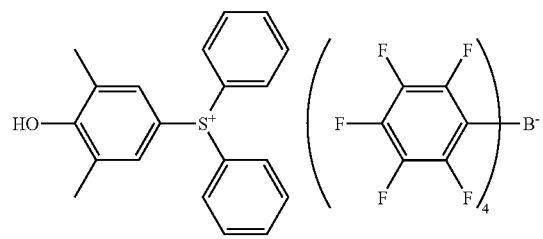
(b-22)
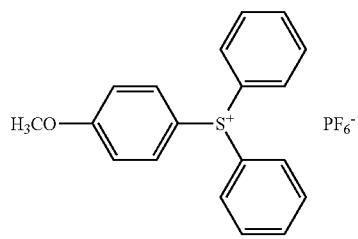
(b-23)
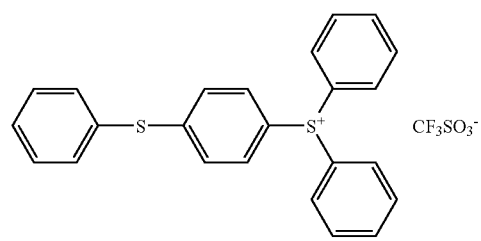
(b-24)
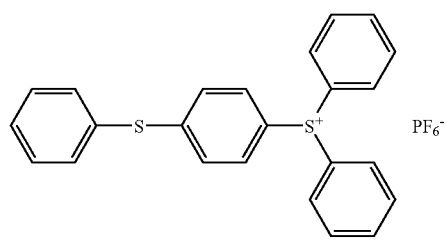
(b-25)
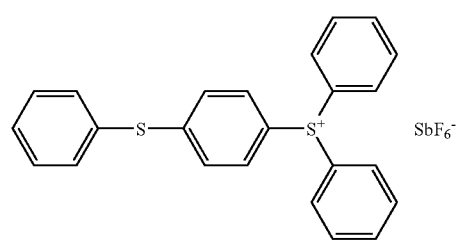
(b-26)
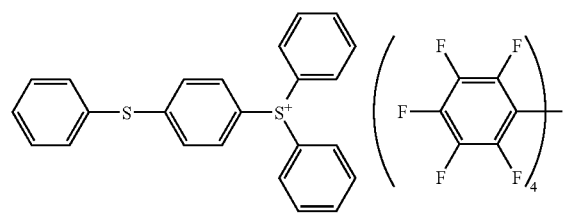
(b-27)
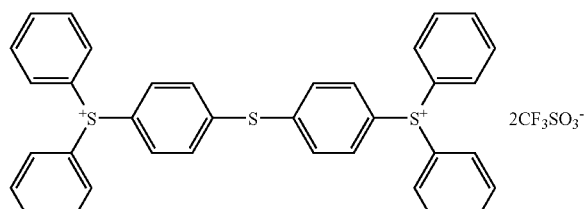
(b-28)
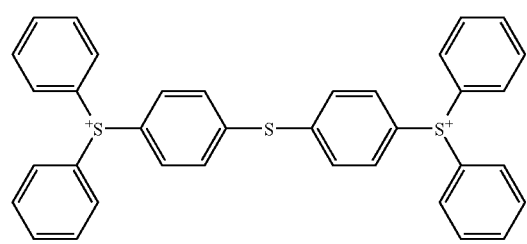
(b-29)
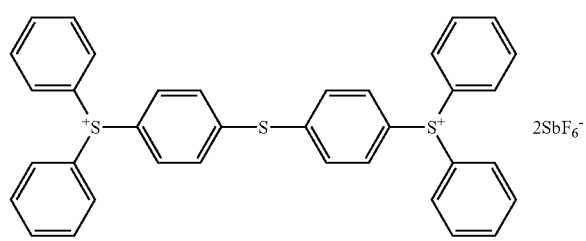
(b-30)
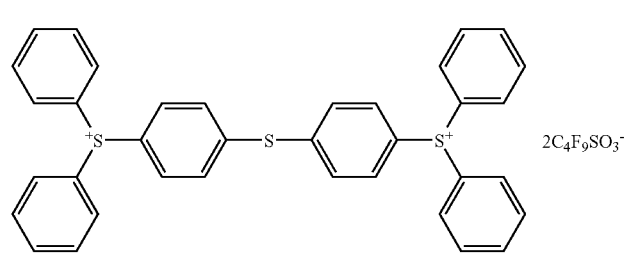
(b-31)

-continued
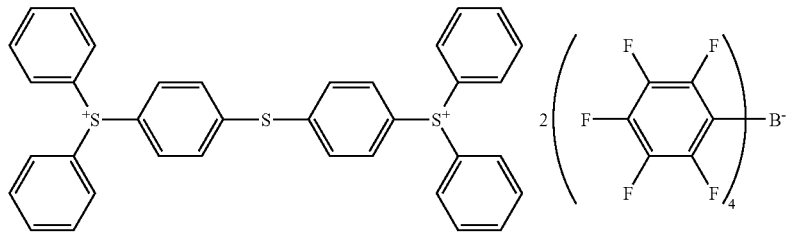
(b-32)
(b-33) (b-34)
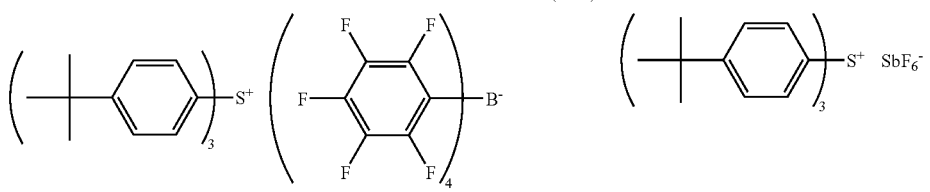
(b-35) (b-36)
(b-37) (b-38)
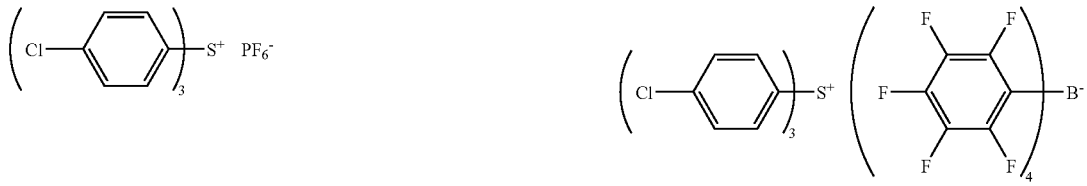
(b-39) (b-40)
(b-41) (b-42)
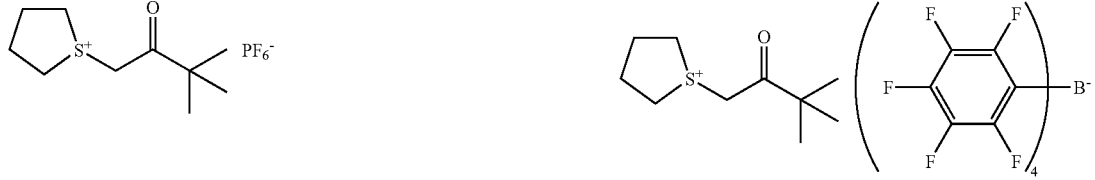
(b-43) (b-44)
(b-45) (b-46)
(b-47) (b-48)

-continued
(b-49) 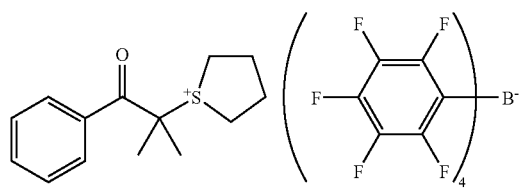
(b-50) 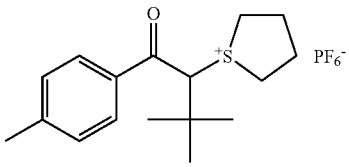
(b-51) 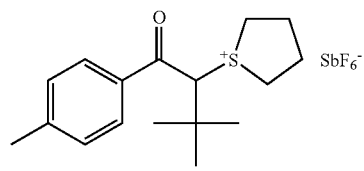
(b-52) 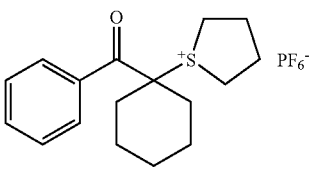
(b-53) 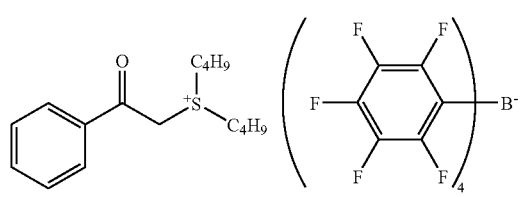
(b-54) 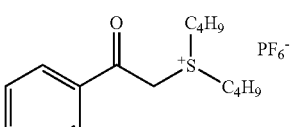
(b-55) 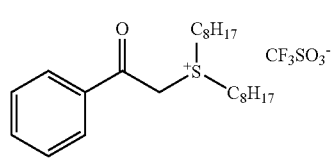
(b-56) 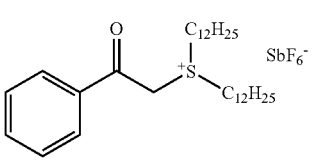
(b-57) 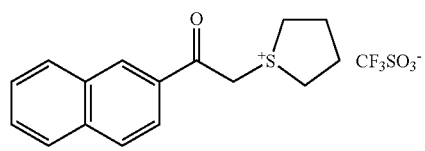
(b-58) 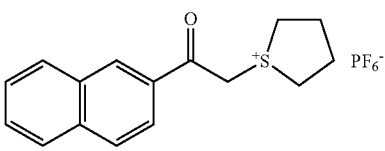
(b-59) 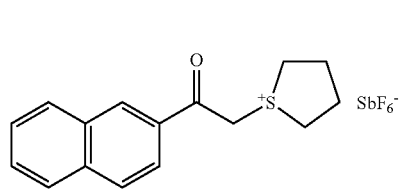
(b-60) 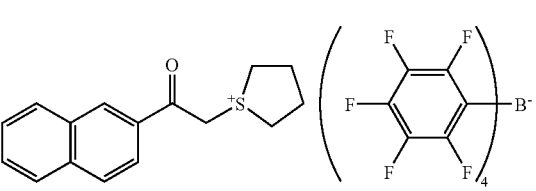
(b-61) 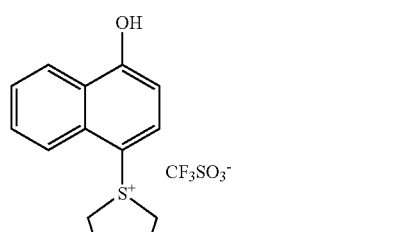
(b-62) 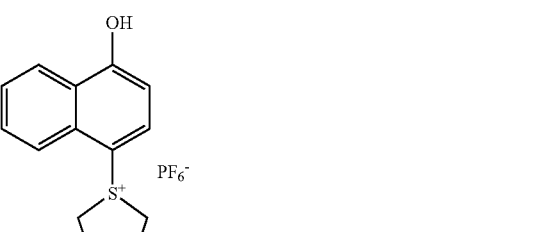
(b-63) 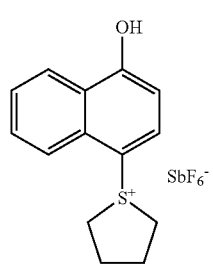
(b-64) 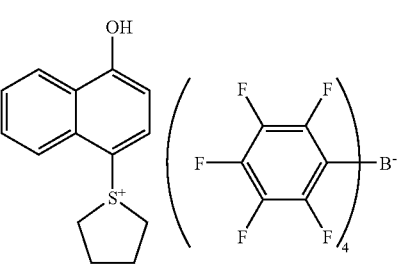

(b-65)
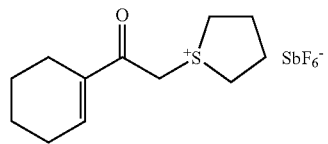
(b-66)
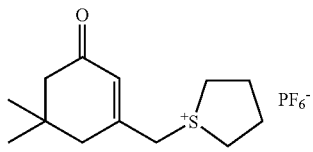
(b-67)
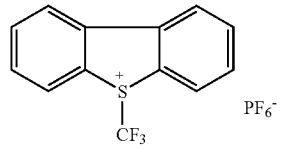
(b-68)
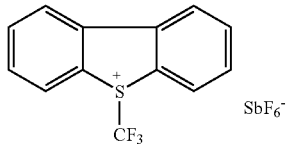
(b-69)
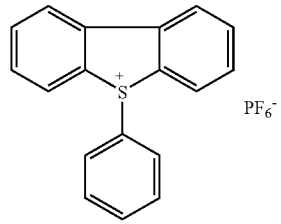
(b-70)
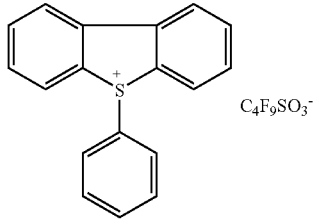
(b-71)
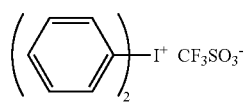
(b-72)
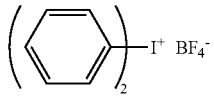
(b-73)
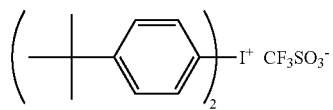
(b-74)
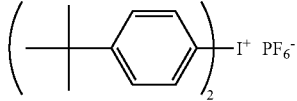
(b-75)
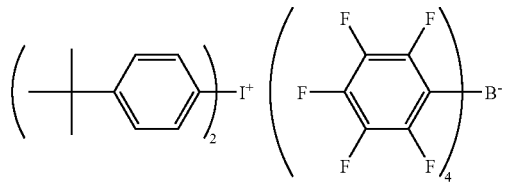
(b-76)
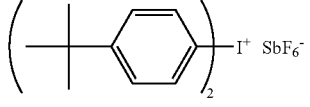
(b-77)
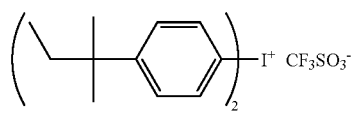
(b-78)
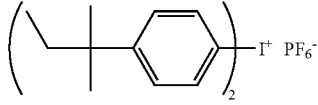
(b-79)
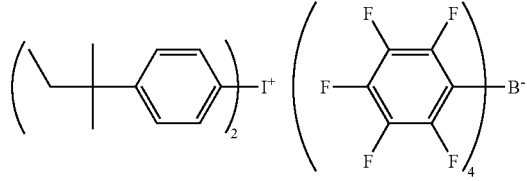
(b-80)
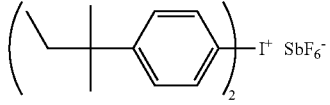
(b-81)
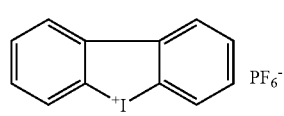
(b-82)
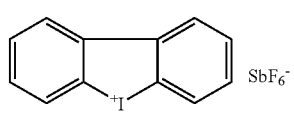
(b-83)
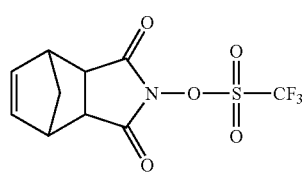
(b-84)
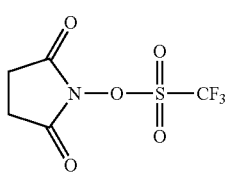

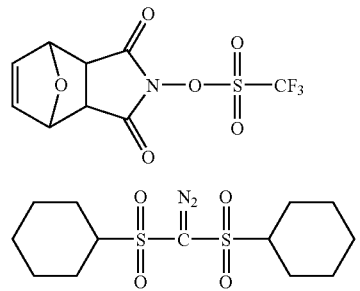
(b-85)

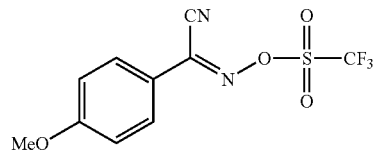
(b-87)

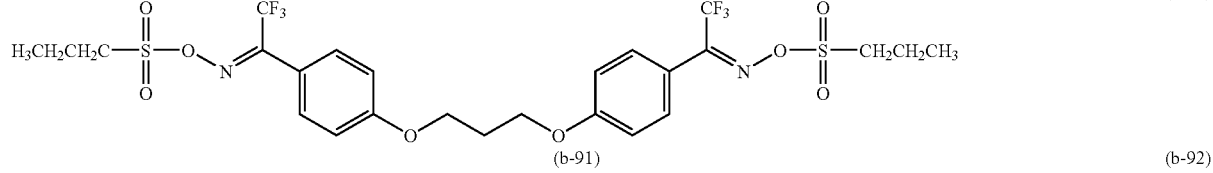
(b-90)

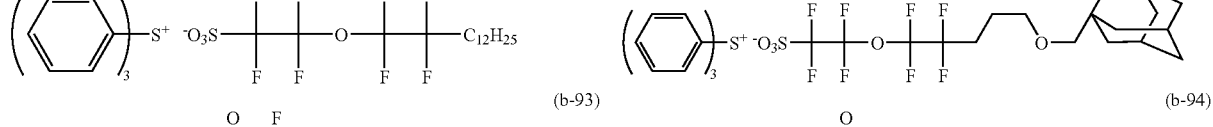
(b-91) (b-92)

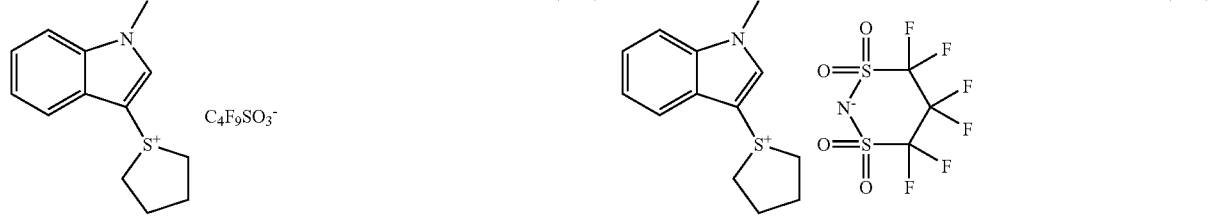
(b-95)

(b-86)

(b-88)

(b-89)

(b-93)

(b-94)

(b-96)

In addition, the oxazole derivatives, s-triazine derivatives and the like described in JP-A No. 2002-122994, paragraph Nos. [0029] to [0030], may also be used favorably.

Further, the onium salt and sulfonate compounds exemplified in JP-A No. 2002-122994, paragraph Nos. [0037] to [0063], may also be used favorably.

The photo acid generating agent may be used alone or in combination of two or more of them.

The content of the photo acid generating agent in the ink composition according to the invention is preferably 0.1 to 20 mass %, more preferably 0.5 to 10 mass %, and further preferably 1 to 7 mass % in terms of the total solid content of the composition.

[Coloring Agent]

The ink composition according to the invention preferably contains a coloring agent for producing a colored image.

The coloring agent useful in the invention is not particularly limited, but is preferably a pigment or an oil soluble dye having excellent weather resistance and color reproducibility, and may be optionally selected from known coloring agents such as solubility dyes. The coloring agent suitable to the ink composition according to the invention preferably does not function as a polymerization inhibitor in the polymerization reaction for curing. This is to prevent the decrease in the sensitivity of the curing reaction by actinic radiation.

[Pigment]

The pigment is not particularly limited, and any one of common commercially available pigments, including organic and inorganic pigments, dispersions of the pigment dispersed in an insoluble resin, and pigments surface-grafted with a resin, may be used. In addition, dyed resin particles may also be used.

Such pigments include the pigments described, for example, in Seijiro Itoh Ed., "Ganryo no Jiten (Dictionary of Pigments)" (2000), W. Herbst K. Hunger, Industrial Organic Pigments", and JP-A Nos. 2002-12607, 2002-188025, 2003-26978, and 2003-342503.

Specific Examples of the organic and inorganic pigments exhibiting yellow color employable in the invention include monoazo pigments such as C.I. Pigment Yellow 1 (Fast Yellow G, etc.) and C.I. Pigment Yellow 74, disazo pigments such as C.I. Pigment Yellow 12 (Disazo Yellow AAA, etc.) and C.I. Pigment Yellow 17, non-benzidine azo pigments such as C.I. Pigment Yellow 180, azolake pigments such as C.I. Pigment Yellow 100 (tartrazine yellow lake, etc.), condensation azo pigments such as C.I. Pigment Yellow 95 (condensation azo yellow GR, etc.), acidic dye lake pigments such as C.I. Pigment Yellow 115 (quinoline yellow lake, etc.), basic dye lake pigments such as C.I. Pigment Yellow 18 (thioflavin lake, etc.), anthraquinone pigments such as fravantrone yellow (Y-24), isoindolinone pigments such as isoindolinone yellow 3RLT (Y-110), quinophtharone pigments such as quinophtharone yellow (Y-138), isoindoline pigments such as isoindoline yellow (Y-139), nitroso pigments such as C.I. Pigment Yellow 153 (nickel nitroso yellow, etc.), metal complex salt azomethine pigments such as C.I. Pigment Yellow 117 (copper azomethine yellow, etc.), and the like.

Examples thereof exhibiting red or magenta color include monoazo pigments such as C.I. Pigment Red 3 (toluidine red, etc.), disazo pigments such as C.I. pigment red 38 (pyrazolone red B, etc.), azolake pigments such as C.I. Pigment Red 53:1 (lake red C, etc.) and C.I. Pigment Red 57:1 (Brilliant Carmine 6B), condensation azo pigments such as C.I. Pigment Red 144 (condensation azo red BR, etc.), acidic dye lake pigments such as C.I. Pigment Red 174 (phloxine B lake, etc.), basic dye lake pigments such as C.I. Pigment Red 81 (rhodamine 6G' lake, etc.), anthraquinone pigments such as C.I. Pigment Red 177 (dianthraquinonyl red, etc.), thioindigo pigments such as C.I. Pigment Red 88 (Thioindigo Bordeaux, etc.), perynone pigments such as C.I. Pigment Red 194 (perynone red, etc.), perylene pigments such as C.I. pigment red 149 (perylene scarlet, etc.), quinacridone pigments such as C.I. Pigment Violet 19 (unsubstituted quinacridone) and C.I. Pigment Red 122 (quinacridone magenta, etc.), isoindolinone pigments such as C.I. Pigment Red 180 (isoindolinone red 2BLT, etc.), alizarin lake pigments such as C.I. Pigment Red 83 (madder lake, etc.), and the like.

Examples thereof exhibiting blue or cyan color include disazo pigments such as C.I. Pigment Blue 25 (dianisidine blue, etc.), phthalocyanine pigments such as C.I. Pigment Blue 15 (phthalocyanine blue, etc.), acidic dye lake pigments such as C.I. Pigment Blue 24 (peacock blue lake, etc.), basic dye lake pigments such as C.I. Pigment Blue 1 (Victria Pure Blue BO lake, etc.), anthraquinone pigments such as C.I. Pigment Blue 60 (indanthron blue, etc.), alkali blue pigments such as C.I. Pigment Blue 18 (alkali Blue V-5:1), and the like.

Examples of the pigment exhibiting green color include phthalocyanine pigments such as C.I. Pigment Green 7 (phthalocyanine green) and C.I. Pigment Green 36 (phthalocyanine green), and azometal complex pigments such as C.I. Pigment Green 8 (nitroso green). Examples of the pigment exhibiting orange color include isoindoline-based pigments such as C.I. Pigment Orange 66 (isoindoline orange), and anthraquinone-based pigments such as C.I. Pigment Orange 51 (dichloropyranthrone orange).

Examples of the pigment exhibiting black color carbon black, titanium black, and aniline black.

Specific examples of the white pigments include basic lead carbonate ($2PbCO_3Pb(OH)_2$, so-called silver white), zinc oxide (ZnO, so-called zinc white), titanium oxide ($TiO_2$, so-called titanium white), and strontium titanate ($SrTiO_3$, so-called titanium strontium white).

Titanium oxide has a lower density and a higher refractive index than other white pigments, is more stable chemically or physically, and thus, has a greater masking and coloring potentials as a pigment, and is excellent in resistance to acid or alkali and other environmental factors. Thus, use of titanium oxide as the white pigment is preferable. Other white pigments (including white pigments other than those described above) may be used as needed.

For dispersing the pigment, any one of dispersing machines, such as ball mill, sand mill, attriter, roll mill, jet mill, homogenizer, paint shaker, kneader, agitator, Henschel mixer, colloid mill, ultrasonic wave homogenizer, pearl mill, and wet jet mill, may be used.

It is also possible to add a dispersant during dispersion of the pigment. Examples of the dispersants include hydroxyl group-containing carboxylic acid esters, salts of a long-chain polyaminoamide with a high-molecular weight acid ester, high-molecular weight polycarboxylic acid salts, high-molecular weight unsaturated acid esters, high-molecular weight copolymers, modified polyacrylates, polyvalent aliphatic carboxylic acids, naphthalenesulfonic acid/formalin condensates, polyoxyethylene alkylphosphoric esters, pigment derivatives, and the like. Use of a commercially available polymer dispersant such as a Solsperse series product manufactured by Zeneca is also preferable.

A dispersion aid suitable for the pigment may be used as a dispersion aid. The dispersant and dispersion aid are preferably added in an amount of 1 to 50 parts by mass with respect to 100 parts by mass of the pigment.

A solvent may be added as the dispersion medium for various components such as pigment in the ink composition or alternatively, the cationic polymerizable compound above, which is a low-molecular weight component, may be used without solvent; but, the ink composition according to the invention preferably contains no solvent, because the composition is a radiation-curing ink that is hardened after application on a recording medium. It is because the solvent remaining in the hardened ink image leads to deterioration in solvent resistance and causes a problem of VOC (Volatile Organic Compound). From the viewpoints above, the cation polymerizable compound is preferably used as the dispersion medium, and selection of a cation polymerizable monomer lowest in viscosity among them is preferable for improvement in dispersibility and processability of the ink composition.

The average diameter of the pigment is preferably in the range of 0.02 to 0.4 µm, more preferably 0.02 to 0.1 µm, and still more preferably 0.02 to 0.07 µm.

The pigment, the dispersant, and dispersion medium are selected and the dispersion and filtration conditions are determined in such a manner that the average diameter of the pigment particles falls in the preferable range above. Control of particle diameter enables prevention of the clogging in head nozzles and preservation of the storage stability, transparency and curing efficiency of ink.

<Dye>

The dye for use in the invention is preferably an oil soluble dye. Specifically, the dye preferably has a solubility in water (mass of the colorant dissolved in 100 g of water) of 1 g or less at 25° C., preferably 0.5 g or less, and more preferably 0.1 g or less. Accordingly, so-called water-insoluble and oil soluble dyes are used favorably.

As for the dyes for use in the invention, it is preferable to introduce an oil-solubilizing group on the basic dye structure described above, to ensure that the dye is dissolved in the amount needed in the ink composition.

Examples of the oil-solubilizing groups include long-chain branched alkyl groups, long-chain branched alkoxy groups, long-chain branched alkylthio groups, long-chain branched alkylsulfonyl groups, long-chain branched acyloxy groups, long-chain branched alkoxycarbonyl groups, long-chain branched acyl groups, long-chain branched acylamino groups, branched alkylsulfonylamino groups, long-chain branched alkylaminosulfonyl groups, as well as aryl, aryloxy, aryloxycarbonyl, arylcarbonyloxy, arylaminocarbonyl, arylaminosulfonyl, and arylsulfonylamino groups containing these long-chain branched substituent groups, and the like.

Alternatively, it is also possible to introduce an oil-solubilizing group, such as alkoxycarbonyl, aryloxycarbonyl, alkylaminosulfonyl or arylaminosulfonyl, on water-soluble dyes containing carboxylic acid or sulfonic acid groups, by using a long-chain branched alcohol, amine, phenol, or aniline derivative.

The melting point of the oil soluble dye is preferably 200° C. or lower, more preferably 150° C. or lower, and further preferably 100° C. or lower. Through the use of an oil soluble dye having a low melting point, crystallization of the dye in the ink composition is suppressed, which improves the storage stability of the ink composition.

The dye preferably has an higher oxidation potential for achieving higher resistance to fading in particular caused by oxidizers such as ozone, and better curing properties. Accordingly, the oxidation potential of the oil soluble dye used in the invention is preferably 1.0 V (vs SCE) or higher, more preferably 1.1 V (vs SCE) or higher, and particularly preferably 1.15 V (vs SCE) or higher.

The yellow dyes having the structure represented by the formula (Y-I) described in JP-A 2004-250483 are preferable.

Example of the dyes particularly preferable include the dyes represented by the formulae (Y-II) to (Y-IV) in JP-A No. 2004-250483, paragraph No. [0034], and typical examples thereof include the compounds described in JP-A No. 2004-250483, paragraph Nos. [0060] to [0071]. The oil soluble dyes represented by the formula (Y-I) described therein may be used not only in yellow ink, but also in inks in any other colors such as black and red.

The compounds having the structures represented by the formulae (3) and (4) in JP-A No. 2002-114930 are preferable as the magenta dyes; and typical examples thereof include the compounds described in JP-A No. 2002-114930, paragraph Nos. [0054] to [0073].

Particularly preferable dyes are the azo dyes represented by the formulae (M-1) to (M-2) in JP-A No. 2002-121414, paragraph Nos. [0084] to [0122], and typical examples thereof include the compounds described in JP-A No. 2002-121414, paragraph Nos. [0123] to [0132]. The oil soluble dyes represented by the formulae (3), (4), and (M-1) to (M-2) may be used not only in magenta ink, but also in inks in any other colors such as black and red inks.

Examples of the cyan dyes include the dyes represented by the formulae (1) to (IV) described in JP-A No. 2001-181547, and the formulae (IV-1) to (IV-4) described in JP-A No. 2002-121414, paragraph Nos. [0063] to [0078], and specific examples thereof include the compounds described in JP-A No. 2001-181547, paragraph Nos. [0052] to [0066], and JP-A No. 2002-121414, paragraph Nos. [0079] to [0081].

Examples of the particularly preferable dyes include the phthalocyanine dyes represented by the formulae (C-I) and (C-II) described in JP-A No. 2002-121414, paragraph Nos. [0133] to [0196], and the phthalocyanine dye represented by the formula (C-II) is even further preferable. Specific examples thereof include the compounds described in JP-A No. 2002-12141, paragraph Nos. [0198] to [0201]. The oil soluble dyes represented by the formulae (I) to (IV), (IV-1) to (IV-4), (C-I), and (C-II) are applicable to any color other than cyan, such as black ink and green ink.

These coloring agents are preferably added to the ink composition in an amount of 1 to 20 mass %, more preferably 2 to 10 mass % as solid matter.

Various additives which may added as needed to the ink composition according to the invention are described below.

[Ultraviolet Absorbent]

An ultraviolet absorbent may be added to the ink composition according to the invention, for improvement in weather fastness and prevention of discoloration of the image obtained.

Examples of the ultraviolet absorbents include the benzotriazole compounds described in JP-A Nos. 58-185677, 61-190537, 2-782, 5-197075 and 9-34057 and others; the benzophenone compounds described in JP-A Nos. 46-2784 and 5-194483, U.S. Pat. No. 3,214,463, and others; the cinnamic acid compounds described in JP-B Nos. 48-30492 and 56-21141, JP-A No. 10-88106, and others; the triazine compounds described in JP-A Nos. 4-298503, 8-53427, 8-239368, 10-182621, and 8-501291, and others; the compounds described in Research Disclosure No. 24239; compounds emitting light by absorbing ultraviolet ray such as stilbene and benzoxazole compounds; so-called fluorescent brighteners; and the like.

The addition amount may be decided suitably according to applications, but is generally, approximately 0.5 to 15 mass % as solid matter.

[Sensitizer]

In the invention, a sensitizer may be added for the purposes of improving the efficiency of acid generation by the photo acid generating agent, and extending the photosensitive wavelength of the agent.

The sensitizer may be any sensitizer which sensitizes the photo acid generating agent through an electron transfer mechanism or an energy transfer mechanism. Preferable examples thereof include fused polycyclic aromatic compounds such as anthracene, 9,10-dialkoxyanthracene, pyrene, and perylene, aromatic ketone compounds such as acetophenone, benzophenone, thioxanthone, and Michler ketone, and heterocyclic compounds such as phenothiazine and N-aryloxazolidinone.

The addition amount is selected properly according to applications, but, and more preferably 0.1 to 0.5 mole % with respect to the photo acid generating agent.

[Antioxidant]

An antioxidant may be added according to the invention, for improvement of stability of the ink composition. Examples of the antioxidants include those described in EP Laid-Open Nos. 223739, 309401, 309402, 310551, 310552, and 459-416, German Patent Laid-Open No. 3435443, JP-A Nos. 54-48535, 62-262047, 63-113536, 63-163351, 2-262654, 2-71262, 3-121449, 5-61166, and 5-119449, U.S. Pat. Nos. 4,814,262 and 4,980,275, and others.

The addition amount is decided properly according to applications, but generally, approximately 0.1 to 8 mass % as solid matter.

[Antifading Agent]

Various types of organic antifading agents and metal complex antifading agents may be used according to the invention.

Examples of the organic antifading agents include hydroquinones, alkoxy phenols, dialkoxy phenols, phenols, anilines, amines, indanes, chromanes, alkoxy anilines, and heterocycles. Examples of the metal complex antifading agents include nickel complexes and zinc complexes. Specific examples thereof include the compounds described in patents cited in Research Disclosure No. 17643, VII, Sections I to J, Research Disclosure No. 15162, Research Disclosure No. 18716, p. 650 left column, Research Disclosure No. 36544, p. 527, Research Disclosure No. 307105, p. 872, and Research Disclosure No. 15162, and the compounds included in the formula of typical compounds and compound examples described in JP-A No. 62-215272, pp. 127-137.

The addition amount is selected properly according to applications, but preferably 0.1 to 8 mass % as solid matter.

[Conductive Salt]

A conductive salt such as potassium thiocyanate, lithium nitrate, ammonium thiocyanate, and dimethylamine hydrochloride may be added according to the invention, for the purpose of controlling the ejection properties.

[Solvent]

Addition of an extremely trace amount of organic solvent to the ink composition according to the invention is effective for improvement in adhesiveness to the recording medium.

Examples of the solvents include ketone solvents such as acetone, methylethylketone, and diethylketone; alcohol solvents such as methanol, ethanol, 2-propanol, 1-propanol, 1-butanol, and tert-butanol; chlorine-based solvents such as chloroform, and methylene chloride; aromatic solvents such as benzene and toluene; ester solvents such as ethyl acetate, butyl acetate, and isopropyl acetate; ether solvents such as diethylether, tetrahydrofuran, and dioxane; glycol ether solvents such as ethylene glycol monomethyl ether and ethylene glycol dimethyl ether; and the like.

In such a case, the amount of the solvent added is in the range that does not cause problems of solvent resistance and VOC, and thus, preferably in the range of 0.1 to 5 mass %, more preferably 0.1 to 3 mass %, in the entire ink composition.

[Polymer Compound]

Various types of polymer compounds may be added according to the invention for the purpose of controlling the physical properties of the film formed by curing. Examples of the polymer compounds include acrylic polymers, polyvinylbutyral resins, polyurethane resins, polyamide resins, polyester resins, epoxy resins, phenol resins, polycarbonate resins, polyvinylbutyral resins, polyvinylformal resins, shellac, vinyl resins, acrylic resins, rubber resin, waxes, other natural resins, and the like. These resins may be used in combination of two or more. Among them, vinyl copolymers obtained by copolymerization with an acrylic monomeric are preferable. In addition, copolymers containing a "carboxyl group-containing monomer", an "alkyl methacrylate ester", or an "alkyl acrylate ester" as the structural unit as a copolymerization component are also used favorably for the polymer binding material.

The surfactants include those described in JP-A Nos. 62-173463 and 62-183457. Examples thereof include anionic surfactants such as dialkylsulfoscuccinic acid salts, alkylnaphthalenesulfonic acid salts, and fatty acid salts; nonionic surfactants such as polyoxyethylene alkylethers, polyoxyethylene alkylallylethers, acetylene glycol, and polyoxyethylene-polyoxypropylene block copolymers; cationic surfactants such as alkylamine salts and quaternary ammonium salts; and the like. An organic fluorocompound may be used instead of the surfactant. The organic fluorocompound is preferably hydrophobic. Examples of the organic fluorocompounds include fluorochemical surfactants, oily fluorochemical compounds (e.g., fluorine oil) and solid fluorochemical compound resins (e.g., tetraethylenefluoride resin); and typical examples thereof include those described in JP-B No. 57-9053 (Columns 8 to 17) and JP-A No. 62-135826.

In addition, a leveling additive, a matting agent, a wax for adjustment of film physical properties, or a tackifier for improvement of the adhesiveness to the recording medium such as of polyolefin and PET that does not inhibit polymerization may be added as needed to the ink composition according to the invention. Typical examples of the tackifiers include the high-molecular weight adhesive polymers described in JP-A 2001-49200, pp. 5 to 6 (e.g., copolymers of a (meth)acrylic ester and an alcohol with an alkyl group having 1 to 20 carbons, of a (meth)acrylic ester and an alicyclic alcohol having 3 to 14 carbons, and of a (meth)acrylic ester and an aromatic alcohol having 6 to 14 carbons), and low-molecular weight adhesive resin containing a polymerizable unsaturated bond, and the like.

Example of Ink Composition

As described above, the ink composition according to the invention contains the specific polymerizable compound, the compound generating an acid by irradiation with a radiation ray, and optionally contains other polymerizable compounds and coloring agents. With respect to the total mass of the ink composition, the content of the coloring agent is preferably 1 to 10 mass %, more preferably 2 to 8 mass %, and the total content of the polymerizable compounds including the specific polymerizable compound is preferably 1 to 97 mass %, more preferably 30 to 95 mass %. The proportion of the compound generating an acid by irradiation with a radiation ray to the total polymerizable compounds including the specific polymerizable compound is preferably 0.01 to 20 mass %, and more preferably 0.1 to 20 mass %.

In cases where the ink composition according to the invention is used as an inkjet recording ink, in consideration of the ejection properties, the viscosity is preferably 7 to 30 mPa·s, and more preferably 7 to 20 mPa·s at the temperature during ejection (for example 40 to 80° C., preferably 25 to 30° C.). For example, the viscosity of the ink composition according to the invention at room temperature (25 to 30° C.) is preferably 35 to 500 mPa·s, and more preferably 35 to 200 mPa·s. The composition ratio of the ink composition according to the invention is preferably adjusted properly in such a manner that the viscosity falls within the above-described range. When the composition is highly viscous at room temperature, ink penetration into a recording medium is avoided even if the recording medium is porous, which allows to reduce the amount of uncured monomers and odors. Further, bleeding of the landed ink droplets is reduced, which results in the improvement of image quality.

The surface tension of the ink composition according to the invention is preferably 20 to 30 mN/m and more preferably 23 to 28 mN/m. When the ink composition according to the invention is used on various recording media such as polyolefin, PET, coated paper, and non-coated paper, the surface tension thereof is preferably 20 mN/m or more for prevention of ink bleeding and penetration, and 30 mN/m or less for improvement in compatibility therewith.

The ink composition according to the invention is favorably used as an inkjet recording ink. In cases where the composition is used as an inkjet recording ink, the ink composition is ejected on a recording medium using an inkjet printer, thereafter the ejected ink composition is cured by irradiation with a radiation ray for recording.

The cured film formed by the ink composition according to the invention has been cured by irradiation with a radiation ray such as ultraviolet light, and has excellent strength. Therefore, outside of using it for image formation, for example, the ink composition is useful for various applications such as formation of an ink receiving layer (image areas) on a planographic printing plate.

<Inkjet Recording Method and Printed Material>

The inkjet recording method to which the ink composition according to the invention is favorably applied (the inkjet recording method according to the invention) is further described below.

The inkjet recording method according to the invention comprises: ejecting the ink composition according to the invention onto a recording medium (for example, a support or a recording material) using an inkjet recording apparatus, and then curing the ink composition by irradiation of the ejected ink composition with actinic radiation. The cured ink composition forms an image on the recording medium.

The recording medium applicable to the inkjet recording method according to the invention is not particularly limited, and examples thereof include papers such as ordinary uncoated paper and coated paper, various unabsorbent resin materials and films thereof used for so-called soft packaging. Examples of the various plastic films include a PET film, an OPS film, an OPP film, an ONy film, a PVC film, a PE film, and a TAC film. Other examples of the plastics useful as the recording medium material include, polycarbonate, acrylic resins, ABS, polyacetal, PVA, and rubbers. Metals and glasses are also useful as the recording medium.

The ink composition according to the invention undergoes less heat shrinkage during curing, and provides excellent adhesiveness to the base material (recording medium). Therefore, the ink composition has the advantage in its capability to form a high definition image even on a film tends to be curled or deformed by curing shrinkage of the ink, or by heat generated during curing reaction of the ink, for example, thermally shrinkable films, a PET film, an OPS film, an OPP film, an ONy film, and a PVC film.

In addition, another examples of the recording material applicable to the invention include the support of the below-described planographic printing plate.

Examples of the actinic radiation applicable to the inkjet recording method according to the invention include α rays, γ rays, X rays, ultraviolet light, visible light, infrared light, and electron beams. The peak wavelength of the actinic radiation is preferably 200 to 600 nm, more preferably 300 to 450 nm, and further preferably 350 to 420 nm. The power of the actinic radiation is preferably 2,000 mJ/cm$^2$ or less, more preferably 10 to 2,000 mJ/cm$^2$, further preferably 20 to 1,000 mJ/cm$^2$, and most preferably 50 to 800 mJ/cm$^2$.

In particular, according to the inkjet recording method according to the invention, the radiation ray is preferably emitted from a light emitting diode which emits ultraviolet light having a emission peak wavelength of 350 to 420 nm and achieving a maximum illumination intensity of 10 to 1,000 mW/cm$^2$ on the surface of the above-described recording medium.

Other conditions applicable to the inkjet recording method according to the invention and details about the inkjet recording apparatus and others will be described below in description of the planographic printing plate according to the invention, a favorable application of the inkjet recording method according to the invention, and the By using the inkjet recording method according to the invention, it is possible to make the dot diameter of ejected ink composition constant and obtain an image improved in quality even on various recording media different in surface wettability. For obtaining a color image in the invention, it is preferable to form images one by one from a color image lower in lightness. If inks are superimposed from the ink lower in lightness, the radiation ray does not easily reach to the lower ink, often leading to deterioration in curing efficiency, increase in the amount of residual monomer, generation of odor, and deterioration in adhesiveness. Although it is possible to irradiate actinic radiation on a full-color image simultaneously, it is preferable to irradiate on each color image formed in sequence for acceleration of curing.

The printed material according to the invention has an image formed thereon using the ink composition according to the invention by the above-described inkjet recording method (the inkjet recording method according to the invention). Therefore, the printed material is of high quality, and has a highly flexible image.

[Planographic Printing Plate and Method of Producing Planographic Printing Plate[Polymer Compound]

The method of producing a planographic printing plate according to the invention is a method of producing a planographic printing plate comprising: ejecting the ink composition according to the invention onto a support, and then curing the ejected ink composition by irradiation of actinic radiation so as to form a hydrophobic image.

The planographic printing plate according to the invention is also a planographic printing plate prepared according to the method of producing a planographic printing plate according to the invention, which has a support and a hydrophobic image formed on the support.

Heretofore, as a planographic printing plate, a so-called PS plate composed of a hydrophilic support having thereon an lipophilic photosensitive resin layer has been widely used. In a method for producing this PS plate, normally, after a mask exposure (surface exposure) is carried out via a lith film, non-exposed areas are dissolved and removed to give a desired printing plate. However, in recent years, a technique of digitizing image information using a computer by electronically processing, storing, and outputting the information has become widespread, and a new image output system that can be used for the above technique has been desired. In particular, a computer to plate (CTP) technique in which a printing plate is directly produced by scanning according to digitized image information with highly coherent light such as laser light without using a lith film has been developed.

As a system for obtaining a planographic printing plate that makes possible the above scanning exposure, a method for directly producing a planographic printing plate using an ink composition can be cited. This method comprises ejecting an ink onto a support (preferably a hydrophilic support) using an inkjet system or the like, and exposing areas having the ink composition to actinic radiation to give a printing plate having a desired image (preferably a hydrophobic image). The ink composition suitable for such a system is the ink composition according to invention.

The steps of the method for producing the planographic printing plate according to the invention are further described below.

<The Step Ejecting the Ink Composition According to the Invention on the Surface of the Support>

[Support]

The support (recording medium) for the planographic printing plate according to the invention is not particularly limited, if it is a dimensionally rigid plate-shaped support. The support is preferably a hydrophilic support. Examples thereof include papers, papers laminated with a plastic material (e.g., polyethylene, polypropylene, or polystyrene), metal plates (e.g., plates of aluminum, zinc, and copper), plastic films (e.g., films of cellulose diacetate, cellulose triacetate, cellulose propionate, cellulose butyrate, cellulose acetate butyrate, cellulose nitrate, polyethylene terephthalate, polyethylene, polystyrene, polypropylene, polycarbonate, and polyvinylacetal), papers or plastic films having a laminated or vapor-deposited layer of the metal described above, and the like. Preferable supports are, for example, polyester films and aluminum plates. Among them, aluminum plates, which are dimensionally stable and relatively cheaper, are preferable.

The aluminum plate is a pure aluminum plate, an alloy plate containing aluminum as a main component and a small amount of a different element, or a thin film of aluminum or an aluminum alloy laminated with a plastic. Examples of the different element contained in the aluminum alloy include silicon, iron, manganese, copper, magnesium, chromium, zinc, bismuth, nickel, and titanium. The content of the different element in the alloy is preferably 10 mass % or less. In the invention, a pure aluminum plate is preferable, but since the production of completely pure aluminum is difficult with the currently available refining technique, aluminum containing a slight amount of foreign elements may be used. The aluminum plate is not specified as to its composition, and may be selected properly from known materials.

The thickness of the support is preferably 0.1 to 0.6 mm, and more preferably 0.15 to 0.4 mm.

In advance of using the aluminum plate, the aluminum plate is preferably subjected to surface treatment such as surface-roughening treatment and anodizing treatment. The surface treatment facilitate enhancing hydrophilicity and ensuring adhesion between the image recording layer and the support. Before surface-roughening the aluminum plate, if desired, degreasing treatment for removing the rolling oil on the surface is performed using a surfactant, an organic solvent, an alkaline aqueous solution or the like.

The aluminum plate is preferably subjected to a surface finishing treatment such as surface-roughening treatment or anodizing treatment before use. Hydrophilicity of the support and adhesion between the image-recording layer and the support are improved by the surface finishing. Before the surface-roughening treatment, the aluminum plate is subjected to a degreasing treatment, for example, with a surfactant, organic solvent, aqueous alkaline solution, or the like for removal of the rolling oil on surface.

Various methods may be used for surface roughening of aluminum plate, and examples thereof include mechanical surface-roughening treatment, electrochemical surface-roughening treatment (surface-roughening by dissolving the surface electrochemically), and chemical surface-roughening treatment (surface-roughening by dissolving the surface chemically).

Any one of the methods known in the art such as ball polishing, brushing, blast polishing, and buffing may be used as the method of mechanical surface-roughening. Alternatively, a transfer method of transferring surface irregularity with a surface-irregular roll during hot rolling of aluminum may be used.

The electrochemical surface-roughening may be performed, for example, by applying an alternate or direct current to the support in an electrolyte solution containing an acid such as hydrochloric acid or nitric acid. Yet alternatively, the method of using a mixed acid described in JP-A No. 54-63902 may also be used.

The aluminum plate after surface-roughening treatment may be etched as needed by using an aqueous solution, for example, of potassium hydroxide or sodium hydroxide, and further after neutralization, treated as needed in an anodizing process for improvement in abrasion resistance.

Various electrolytes forming a porous oxide film may be used as the electrolytes for use in the process of anodizing aluminum plate. Sulfuric acid, hydrochloric acid, oxalic acid, chromic acid, or a mixed acid thereof is used commonly. The concentration of the electrolyte is determined properly according to the kind of electrolyte.

The condition of the anodizing process varies according to the electrolyte used, and thus is not specified particularly; but generally, the electrolyte concentration is 1 to 80 mass %; liquid temperature, 5 to 70° C.; electric current density, 5 to 60 A/dm$^2$ voltage, 1 to 100 V; and electrolysis period, 10 seconds to 5 minutes. The amount of the anodic oxide film formed is preferably 1.0 to 5.0 g/m$^2$ and more preferably 1.5 to 4.0 g/m$^2$. Favorably in the range above, it is possible to obtain a planographic printing plate favorable in printing durability and scuff resistance in the nonimage area.

The surface-finished support having an anodic oxide film described above may be used as the support for use in the invention, but may be subjected to another treatment as needed, for example, the treatment for expanding or sealing the micropores in the anodic oxide film described in JP-A Nos. 2001-253181 and 2001-322365 or a surface hydrophilizing treatment of immersing it in an aqueous solution containing a hydrophilic compound, for further improvement in adhesion to the upper layer, hydrophilicity, staining resistance, heat insulation efficiency, and others. The expanding and sealing treatments are not limited to the methods described above, and any one of known methods may be used.

<Micropore Sealing Treatment>

Micropore sealing may carried out in steam, or in fluorozirconic acid alone, an aqueous solution containing an inorganic fluorine compound such as sodium fluoride, steam containing lithium chloride, or heat water. Among them, micropore sealing in an aqueous solution containing an inorganic fluorine compound, water vapor, or heat water is preferable. The methods are respectively described below.

—Micropore Sealing in an Aqueous Solution Containing an Inorganic Fluorine Compound—

The inorganic fluorine compound used in micropore sealing in an aqueous solution containing an inorganic fluorine compound is preferably a metal fluoride.

Examples thereof include sodium fluoride, potassium fluoride, calcium fluoride, magnesium fluoride, sodium fluorozirconate, potassium fluorozirconate, sodium fluorotitanate, potassium fluorotitanate, ammonium fluorozirconate, ammonium fluorotitanate, potassium fluorotitanate, fluorozirconic acid, fluorotitanic acid, hexafluorosilicic acid, nickel fluoride, iron fluoride, fluorophosphoric acid, and ammonium fluorophosphate. Among them, sodium fluorozirconate, sodium fluorotitanate, fluorozirconic acid, and fluorotitanic acid are preferable.

The concentration of the inorganic fluorine compound in the aqueous solution is 0.01 mass % or more, and more preferably 0.05 mass % or more to sufficiently seal the micropores on the anodized film, and preferably 1 mass % or less, and more preferably 0.5 mass % or less from the viewpoint of stain resistance.

The aqueous solution containing an inorganic fluorine compound preferably further contains a phosphate compound. The inclusion of a phosphate compound is preferable because it improves hydrophilicity on the surface of the anodized film, on-machine developability, and stain resistance.

Preferable examples of the phosphate compound include metal phosphates such as alkali metal phosphates and alkaline earth metal phosphates.

Specific examples thereof include zinc phosphate, aluminum phosphate, ammonium phosphate, diammonium hydrogen phosphate, ammonium dihydrogen phosphate, monoammonium phosphate, monopotassium phosphate, monosodium phosphate, potassium dihydrogen phosphate, dipotassium hydrogen phosphate, calcium phosphate, ammonium sodium hydrogen phosphate, magnesium hydrogen phosphate, magnesium phosphate, ferrous phosphate, ferric phosphate, sodium dihydrogen phosphate, sodium phosphate, disodium hydrogen phosphate, lead phosphate, diammonium phosphate, calcium dihydrogen phosphate, lithium phosphate, phosphotungstic acid, ammonium phosphotungstate, sodium phosphotungstate, ammonium phosphomolybdate, sodium phosphomolybdate, sodium phosphite, sodium tripolyphosphate and sodium pyrophosphate. Of these phosphate compounds, sodium dihydrogen phosphate, disodium hydrogen phosphate, potassium dihydrogen phosphate and dipotassium hydrogen phosphate are preferred over the others. Among them, sodium dihydrogen phosphate, disodium hydrogen phosphate, potassium dihydrogen phosphate, and dipotassium hydrogen phosphate are preferable. The combination of an inorganic fluorine compound and a phosphate compound not particularly limited, but it is preferable that the aqueous solution contain sodium fluorozirconate as the inorganic fluorine compound and at least sodium dihydrogen phosphate as the phosphate compound.

The concentration of the phosphate compound in the aqueous solution is preferably 0.01 mass % or more, and more preferably 0.1 mass % or more from the viewpoints of on-machine developability and stain resistance, and preferably 20 mass % or less, and more preferably 5 mass % or less from the viewpoint of solubility.

The proportion between the compounds in the aqueous solution is not particularly limited, but the mass ratio between the inorganic fluorine compound and the phosphate compound is preferably 1/200 to 10/1, and more preferably 1/30 to 2/1.

The temperature of the aqueous solution is preferably 20° C. or more, and more preferably 40° C. or more, besides preferably 100° C. or less, and more preferably 80° C. or less.

The pH of the aqueous solution is preferably 1 or more, and more preferably 2 or more, besides preferably 11 or less, and more preferably 5 or less.

The method for micropore sealing in an aqueous solution containing an inorganic fluorine compound is not particularly limited, and examples thereof include a immersion method and a spray method. Operations in these methods may be performed once or more than once individually, or those methods may be used in combination.

Among the methods, the immersion method is preferable. In cases where the immersion method is used for the treatment, the treatment time is preferably 1 second or more, more preferably 3 seconds or more, besides preferably 100 seconds or less, and more preferably 20 seconds or less.

—Micropore Sealing in Steam—

The micropore sealing in steam can be performed, for example, by bringing steam under elevated or normal pressure into contact with the anodic oxide film continuously or uncontinuously.

The temperature of the steam is preferably 80° C. or higher, more preferably 95° C. or higher, and preferably 105° C. or lower.

The pressure of the steam is preferably in the range of (atmospheric pressure—50 mm Aq) to (atmospheric pressure +300 mm Aq), or ($1.008 \times 10^5$ to $1.043 \times 10^5$ Pa).

The contact time of the steam is preferably 1 second or more, more preferably 3 seconds or more and preferably 100 seconds or less, more preferably 20 seconds or less.

—Micropore Sealing in Hot Water—

The micropore sealing in steam is performed, for example, by immersing an aluminum plate carrying a formed anodic oxide film in hot water. The hot water may contain an inorganic salt (e.g., phosphate salt) or an organic salt.

The temperature of the hot water is preferably 80° C. or higher, more preferably 95° C. or higher, and preferably 100° C. or lower. The period of immersion in hot water is preferably 1 second or more, more preferably 3 seconds or more, and preferably 100 seconds or less, more preferably 20 seconds or less.

The hydrophilizing treatments for use in the invention include the alkali metal silicate methods described in U.S. Pat. Nos. 2,714,066, 3,181,461, 3,280,734 and 3,902,734. In the method, the support is immersed and electrolyzed, for example, in an aqueous solution of sodium silicate. Also included are the method of treating the support with potassium fluorozirconate described in JP-B No. 36-22063 and the methods of treating it with polyvinylphosphonic acid described in U.S. Pat. Nos. 3,276,868, 4,153,461 and 4,689,272.

The support preferably has an average center-line roughness of 0.10 to 1.2 μm. Favorably in the range above, it is possible to obtain desirable adhesiveness to the image-recording layer, favorable printing durability, and favorable staining resistance.

In ejecting the ink composition according to the invention on the surface of the hydrophilic support above, it is preferably to heat the ink composition to a temperature of preferably 40 to 80° C., more preferably 25 to 30° C. and thus lower the viscosity of the ink composition to preferably 7 to 30 m Pa·s, more preferably 7 to 20 m Pa·s. In particular, use of an ink composition having an ink viscosity of 35 to 500 mP·s at 25° C. is preferable as it give a better effect. Use of the method provides high ejection stability.

Commonly, radiation-curing ink compositions including the ink composition according to the invention have higher viscosity than aqueous inks normally used ink compositions, and the viscosity thereof varies significantly according to the fluctuation of temperature during ejection. The fluctuation of the ink viscosity has great influences on the change of droplet size and droplet ejection speed, consequently leading to deterioration in image quality. Thus, it is necessary to keep the temperature during ink ejection as constant as possible. Thus, the control width of the temperature in the invention is preferably temperature setting ±5° C., more preferably temperature setting ±2° C., and still more preferably temperature setting ±1° C.

[Inkjet Recording Apparatus]

The inkjet recording apparatus used in the invention is not particularly limited, and any one of commercially available inkjet recording apparatuses may be used. That is, in the invention, an image may be recorded on a recording medium by using a commercially available inkjet recording apparatus.

The inkjet recording apparatus used in the invention has, for example, an ink-supplying system, a temperature sensor, and a radiation ray source.

The ink-supplying system further has, for example, a stock tank storing an inkjet composition, a supply pipe, an inkjet composition-supplying tank immediately before the inkjet head, a filter, and a piezoelectric inkjet head. The piezoelectric inkjet head allows ejection of multi-sized dots in amounts of 1 to 100 pl, preferably, 8 to 30 pl, at a definition, for example, of 320×320 to 4,000×4,000 dpi, preferably 400× 400 to 1,600×1,600 dpi, and more preferably 720×720 dpi. The "dpi" in the invention means the dot number per 2.54 cm.

As described above, since a radiation curable ink preferably has a constant temperature at the time of ejection, the section from the ink supply tank to the inkjet head may be thermally insulated and heated. The method for controlling the temperature is not limited, and preferable examples thereof include a method of providing a plurality of temperature sensors in piping areas, thereby controlling the temperature in accordance with the ink flow and the environmental temperature. The temperature sensors may be provided on the ink supply tank and in the vicinity of the nozzle of the inkjet head. The head unit to be heated is preferably thermally blocked or insulated. In order to reduce the warm-up time of the printer, or reduce the heat energy loss, it is preferable that the head unit be thermally insulated from other sections, and the thermal capacity of the whole unit to be heated be preferably smaller.

<Forming a Hydrophobic Image on the Surface of a Support by Irradiating the Ejected Ink Composition with Actinic Radiation to Cure the Ink Composition>

The ink composition ejected onto the surface of a hydrophilic support is cured by irradiation with actinic radiation. At this time, if there is a sensitizing dye present together with a polymerization initiator (photoinitiator) in the ink composition, then the sensitizing dye in the system is activated into an excited state by absorption of the actinic radiation, accelerating decomposition of the polymerization initiator upon contact with the polymerization initiator, and a more sensitive curing reaction may be achieved.

Examples of the actinic radiation used herein include α rays, γ rays, electron beam, X rays, ultraviolet light, visible light, and infrared light. Although the peak wavelength of the actinic radiation varies according to the absorption properties of the sensitizing dye, but is, for example, 200 to 600 nm, preferably 300 to 450 nm, and more preferably 350 to 420 nm. In the invention, the polymerization initiating system has sufficient sensitivity even to a low power actinic radiation. Accordingly, the power of the actinic radiation as irradiation energy is, for example, 2,000 mJ/cm$^2$ or less, preferably from 10 to 2,000 mJ/cm$^2$, more preferably from 20 to 1,000 mJ/cm$^2$, and further preferably from 50 to 800 mJ/cm$^2$. Further, the actinic radiation is applied so that the illumination intensity on the exposed surface is, for example, from 10 to 2,000 mW/cm$^2$, and preferably from 20 to 1,000 mW/cm$^2$.

Mercury lamps, gas or solid state lasers and the like have been widely used as actinic radiation sources, and mercury lamps and metal halide lamps are widely used in ultraviolet-curing inkjet printers. However, under the current urgent need for mercury-free devices from the viewpoint of environmental protection, substitution thereof with a GaN semiconductor ultraviolet ray-emitting device is very useful industrially or environmentally. In addition, LED's (UV-LEDs) and LD's (UV-LDs) are smaller in size, longer in lifetime, higher in efficiency and lower in cost, and thus, attracting attention as a light source for radiation-curing inkjet printers.

In the invention, light-emitting diodes (LED) and laser diodes (LD) may be used as the source of actinic radiation. In particular, when a UV light source is needed, a UV-LED or a UV-LD may be used. For example, Nichia Corporation has marketed a violet LED having a wavelength of the main emission spectrum of between 365 nm and 420 nm. Further, when a shorter wavelength is needed, U.S. Pat. No. 6,084,250 discloses an LED capable of emitting actinic radiation whose wavelength is centered between 300 nm and 370 nm. Further, another violet LED is available, and irradiation can be carried out with radiation of a different UV bandwidth. The actinic radiation source particularly preferable in the invention is a UV-LED, and a UV-LED having a peak wavelength at 350 to 420 nm is particularly preferable. The maximum illumination intensity of the LED on a recording medium is preferably 10 to 2,000 mW/cm$^2$, more preferably 20 to 1,000 mW/cm$^2$, and particularly preferably 50 to 800 mJ/cm$^2$.

In the invention, the ink composition is preferably exposed to the actinic radiation, for example, for 0.01 to 120 seconds, preferably, 0.1 to 90 seconds.

The irradiation condition and the basic irradiation method of the actinic radiation are disclosed in JP-A No. 60-132767. Specifically, the exposure is performed in a so-called shuttle process, i.e., by moving a head unit and light sources that are placed at both sides of the head unit in the ink-ejecting device. The actinic radiation is irradiated after a certain period (e.g., 0.01 to 0.5 second, preferably 0.01 to 0.3 second, and more preferably, 0.01 to 0.15 second) from ink ejection. It is possible to prevent bleeding of the ink ejected on the recording medium before curing by controlling the period from ink ejection as short as possible. In this manner, it becomes possible to irradiate the ink before penetration into the depth to which no light is penetrable even on a porous recording medium, suppress the amount of unreacted residual monomer, and consequently reduce odor.

Alternatively, the ink may be hardened with a light from another fixed light source. WO 99/54415 Pamphlet discloses, as the irradiation method, a method of using optical fiber and a method of irradiating the recorded area with a collimated UV ray, i.e., a collimated light reflected from a mirror placed on the side face of head unit.

Thus, by using the method for producing a planographic printing plate according to the invention, a hydrophobic image is formed on the surface of a support by curing the ink composition according to the invention by irradiation with actinic radiation.

As described above, according to an aspect of the invention, there is provided an ink composition which is cured highly sensitively by actinic radiation to form an image having flexibility and excellent adhesiveness to the substrate.

From these facts, the planographic printing plate obtained by the method of producing a planographic printing plate according to the invention (planographic printing plate according to the invention) has a high quality image area having excellent flexibility, and provides excellent printing durability.

EXAMPLES

The invention is illustrated with reference to the following Examples and Comparative Examples. However, the invention is not limited these Examples.

Example 1

<Ink Preparation>

| <Yellow ink 1> | |
|---|---|
| C.I. Pigment Yellow 13 | 5 parts by mass |
| Photocationic polymerization initiator: triphenyl sulfonium salt (trade name: UVI-6992, manufactured by The Dow Chemical Company) | 6 parts by mass |
| Sensitizing dye: 9,10-dibutoxyanthracene | 3 parts by mass |
| Polymerizable compound | |
| Monomer: 3,7-bis(3-oxetanyl)-5-oxanonane (trade name: OXT-221, manufactured by Toagosei Co., Ltd.) | 26 parts by mass |
| Monomer: 3-ethyl-3-phenoxymethyloxetane (trade name: OXT-211, manufactured by Toagosei Co., Ltd.) | 50 parts by mass |
| Monomer: Compound (a-1) shown below | 10 parts by mass |

a-1

| <Magenta ink 1> | |
|---|---|
| C.I. Pigment Red 57:1 | 5 parts by mass |
| Photocationic polymerization initiator: triphenyl sulfonium salt (trade name: UVI-6992, manufactured by The Dow Chemical Company) | 6 parts by mass |
| Sensitizing dye: 9,10-dibutoxyanthracene | 3 parts by mass |
| Polymerizable compound | |
| Monomer: 3,7-bis(3-oxetanyl)-5-oxanonane (trade name: OXT-221, manufactured by Toagosei Co., Ltd.) | 26 parts by mass |
| Monomer: 3-ethyl-3-phenoxymethyloxetane (trade name: OXT-211, manufactured by Toagosei Co., Ltd.) | 50 parts by mass |
| Monomer: compound (a-1) | 10 parts by mass |

| <Cyan ink 1> | |
|---|---|
| C.I. Pigment Blue 15:3 | 5 parts by mass |
| Photocationic polymerization initiator: triphenyl sulfonium salt (trade name: UVI-6992, manufactured by The Dow Chemical Company) | 6 parts by mass |
| Sensitizing dye: 9,10-dibutoxyanthracene | 3 parts by mass |
| Polymerizable compound | |
| Monomer: 3,7-bis(3-oxetanyl)-5-oxanonane (trade name: OXT-221, manufactured by Toagosei Co., Ltd.) | 26 parts by mass |
| Monomer: 3-ethyl-3-phenoxymethyloxetane (trade name: OXT-211, manufactured by Toagosei Co., Ltd.) | 50 parts by mass |
| Monomer: compound (a-1) | 10 parts by mass |

| <Black ink 1> | |
|---|---|
| C.I. Pigment Black 7 | 5 parts by mass |
| Photocationic polymerization initiator: triphenyl sulfonium salt (trade name: UVI-6992, manufactured by The Dow Chemical Company) | 6 parts by mass |
| Sensitizing dye: 9,10-dibutoxyanthracene | 3 parts by mass |
| Polymerizable compound | |
| Monomer: 3,7-bis(3-oxetanyl)-5-oxanonane (trade name: OXT-221, manufactured by Toagosei Co., Ltd.) | 26 parts by mass |
| Monomer: 3-ethyl-3-phenoxymethyloxetane (trade name: OXT-211, manufactured by Toagosei Co., Ltd.) | 50 parts by mass |
| Monomer: compound (a-1) | 10 parts by mass |

Crude color ink 1 of each color prepared as described above was filtered through a filter having an absolute filtration accuracy of 2 μm. Thus, ink composition 1 of each color was obtained.

<<Inkjet Image Recording>>

Next, using the ink composition obtained above, recording on a recording medium was performed with a commercially available inkjet recording apparatus having a piezoelectric inkjet nozzle. The ink supply system was composed of a main tank, a supply pipe, an ink supply tank immediately before an inkjet head, a filter, and a piezoelectric inkjet head, and the section from the ink supply tank to the inkjet head was thermally insulated and heated. Temperature sensors were provided on the ink supply tank and in the vicinity of the nozzle of the inkjet head, and the temperature was controlled so that the nozzle section was always at 70° C.±2° C. The piezoelectric inkjet head was driven so as to discharge multisize dots of 8 to 30 pl at a resolution of 720×720 dpi. After the dots have impacted, the exposure system, the main scanning speed, and the discharge frequency were adjusted so that UV light was focused to give an illumination intensity of 100 mW/cm² on the exposed surface and so that irradiation was started 0.1 seconds after the ink impacted onto the recording medium. Furthermore, the exposure time was made variable, and necessary exposure energy for curing was irradiated. The term dpi referred to in the invention represents the number of dots per inch (~2.54 cm).

<Color Image Formation and Evaluation>

The ink of each color prepared above were discharged in the order black, cyan, magenta, and yellow at an environmental temperature of 25° C., and each color was irradiated with UV rays using a metal halide lamp (trade name: VZERO 085; manufactured by Integration Technology).

The total exposure energy per color was 100 mJ/cm² for all the colors, an energy level that could completely cure the inks to the point where tackiness to the touch disappeared.

As recording media, a grained aluminum support, a transparent biaxially orientated polypropylene film whose surface had been treated so as to be printable, a PVC sheet (trade name: MPI 1005, 2 mm PVC vinyl, manufactured by Avery), a cast coated paper, and a commercially available recycled paper were used. Color Images were recorded on these recording media, and images having a high resolution with no dot bleeding were obtained in all cases. Further, for high quality paper, the ink did not penetrate to the reverse side, the ink was sufficiently cured, and there was hardly any odor due to unreacted monomer. Moreover, the images recorded on the film had sufficient flexibility, did not crack when bent, and there were no problems therewith in an adhesion test involving peeling with Sellotape®.

Example 2

<Magenta Ink 2>

Magenta ink 2 was prepared in the same manner as the magenta ink 1 except that 10 parts by mass of the specific polymerizable compound (a-1), which is one of the monomers used as the polymerizable compound, were changed to 10 parts by mass of the specific polymerizable compound (a-2) shown below.

Example 3

<Magenta Ink 3>

Magenta ink 3 was prepared in the same manner as the magenta ink 1 except that 10 parts by mass of the specific polymerizable compound (a-1), which is one of the monomers used as the polymerizable compound, were changed to 10 parts by mass of the specific polymerizable compound (a-3) shown below.

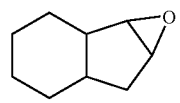

Example 4

<Magenta Ink 4>

Magenta ink 4 was prepared in the same manner as the magenta ink 1 except that 10 parts by mass of the specific polymerizable compound (a-1), which is one of the monomers used as the polymerizable compound, were changed to 10 parts by mass of the specific polymerizable compound (a-4) shown below.

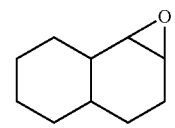

Example 5

<Magenta Ink 5>

Magenta ink 5 was prepared in the same manner as the magenta ink 1 except that 3 parts by mass of "9,10-dibutoxy-anthracene" used as the sensitizing dye were changed to 3 parts by mass of "DAROCUR ITX (manufactured by Ciba Specialty Chemicals)".

Example 6

<Magenta Ink 6>

Magenta ink 6 was prepared in the same manner as the magenta ink 1 except that 5 parts by mass of "C.I. Pigment Red 57:1" were changed to 5 parts by mass of the "oil soluble dye M-1 (oxidation potential +1.37 V)" shown below.

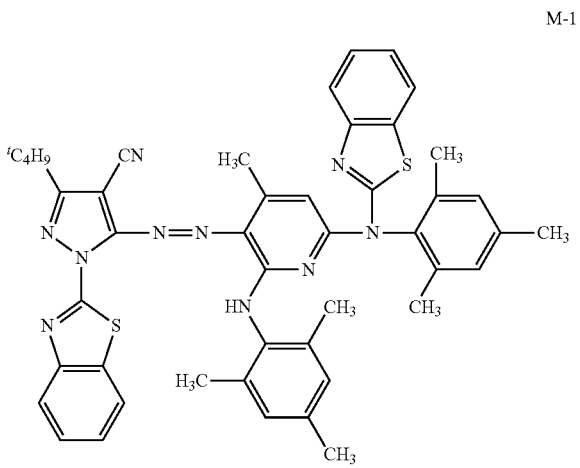

Example 7

<Magenta Ink 7>

Magenta ink 7 was prepared in the same manner as the magenta ink 1 except that 5 parts by mass of "C.I. Pigment Red 57:1", which was used in the magenta ink prepared in the Example 1, were changed to 5 parts by mass of the "oil soluble dye M-2 (oxidation potential +0.94 V)" shown below.

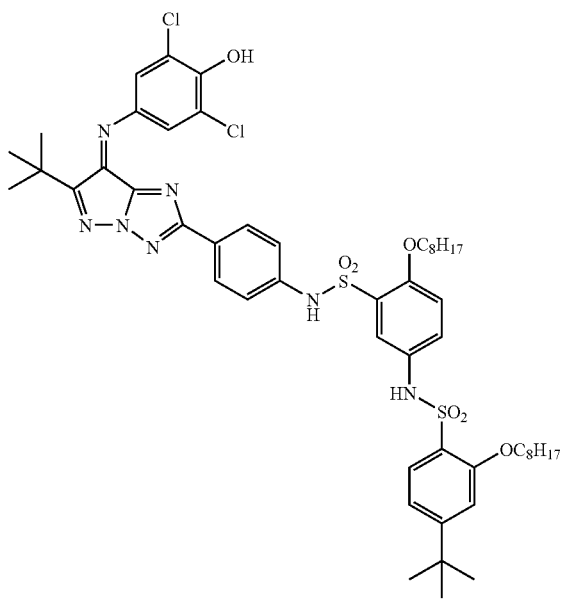

Comparative Example 1

<Magenta Ink 8>

Magenta ink 8 was prepared in the same manner as the magenta ink 1 except that 10 parts by mass of the compound (a-1), which is one of the monomers used as the polymerizable compound, were changed to 10 parts by mass of the comparative compound shown below.

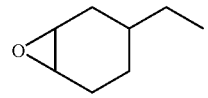

Comparative Example 2

<Magenta Ink 9>

Magenta ink 9 was prepared in the same manner as the magenta ink 1 except that 10 parts by mass of the compound (a-1), which is one of the monomers used as the polymerizable compound, were changed to 10 parts by mass of a monomer: 1,2:8,9 diepoxylimonene (trade name: CELLOXIDE 3000, manufactured by Daicel-UCB Company, Ltd.).

Each of the crude magenta inks 2 to 9 prepared in Examples 2 to 7 and Comparative Examples 1 and 2 was filtered through a filter having an absolute filtration accuracy of 2 μm. Thus, magenta inks 2 to 9 were obtained.

The ink viscosity of the ink compositions prepared in the Examples and Comparative Examples was from 7 to 20 mPa·s at the ink ejection temperature.

<Inkjet Image Recording>

A magenta image was formed in the same manner as Example 1 using each of the magenta inks 2 to 9 of Examples 2 to 7 and Comparative Examples 1 and 2, and the magenta ink 1 of Example 1.

<Inkjet Image Evaluation>

Each of the image formed on the PVC sheet, one of the above-described recording media, was evaluated for the curing sensitivity, flexibility, and adhesiveness according to the methods described below. These measurement methods are further described below.

(Curing Sensitivity Measurement)

On the image surface after ultraviolet irradiation, the exposure energy intensity (mJ/cm$^2$) which makes the image surface non-tacky was defined as the curing sensitivity. The smaller the value, the higher the sensitivity.

(Flexibility Measurement)

Flexibility was evaluated on the basis of the degree of cracks occurred on the cured film after bending the PVC sheet ten times. The bending test was performed using a five point scale with a score of 5 given for the state having absolutely no crack. Scores of 3 or more were evaluated as a practically acceptable state.

(Adhesiveness Measurement)

The adhesiveness to the PVC sheet was evaluated on the basis cross hatch test (EN ISO 2409). Regarding the test, a higher value is more favorable, and scores of 3B or more are evaluated as a practically acceptable state.

TABLE 1

| | Magenta ink number | Sensitivity (mJ/cm$^2$) (mJ/cm$^2$) | Flexibility | Adhesiveness |
|---|---|---|---|---|
| Example 1 | 1 | 165 | 5 | 5B |
| Example 2 | 2 | 165 | 5 | 5B |
| Example 3 | 3 | 165 | 5 | 5B |
| Example 4 | 4 | 165 | 5 | 5B |
| Example 5 | 5 | 165 | 5 | 5B |
| Example 6 | 6 | 165 | 5 | 5B |
| Example 7 | 7 | 165 | 5 | 5B |

TABLE 1-continued

| | Magenta ink number | Sensitivity (mJ/cm$^2$) (mJ/cm$^2$) | Flexibility | Adhesiveness |
|---|---|---|---|---|
| Comparative example 1 | 8 | 800 | 3 | 1B |
| Comparative example 2 | 9 | 400 | 2 | 2B |

As is evident from Table 1, in comparison with Comparative Examples 1 and 2, the ink composition according to the invention was more highly sensitively cured, and formed a cured image having excellent flexibility on the polystyrene substrate, and provided excellent adhesiveness between the polystyrene substrate and the cured image.

Example 8

Image Formation Using Light Emitting Diodes (LEDs)

Inkjet image recording was performed using the magenta ink 1 prepared in Example 1 and in the same manner as Example 1, except that ultraviolet emitting diodes (UV-LED) were used in place of the metal halide lamp (trade name: Vzero 085; manufactured by Integration Technology).

In this embodiment, a NCCU033 (trade name) manufactured by Nichia Corporation was used as the UV-LEDs. The LEDs emit ultraviolet light at a wavelength of 365 nm from a single chip, and about 100 mW of light is emitted from a single chip upon application of a current of about 500 mA. Plural thereof were aligned at intervals of 7 mm to give a power of 0.3 W/cm$^2$ on the surface of a recording medium (hereinafter, sometimes referred to, for convenience, as a medium). The time from impacting to exposure, and the exposure time can be varied by the conveying speed of the medium and the distance in the conveying direction between the head and the LED. In this embodiment, exposure was performed about 0.5 seconds after impacting.

The exposure energy on the recording medium can be adjustable in the range 0.01 to 15 J/cm$^2$ according to the distance from the medium and the conveying speed.

Comparative Example 3

Image Formation Using Light Emitting Diode (LED)

Inkjet image recording was performed in the same manner as Example 8 except that the magenta ink 8 prepared in Comparative Example 1 was used in place of the magenta ink 1 prepared in Example 8.

<Inkjet Image Evaluation>

Each of the inks of Example 8 and Comparative Example 3 was evaluated for the curing sensitivity, flexibility, and adhesiveness in accordance with the above-described method. The results of the evaluations are shown in Table 2.

TABLE 2

| | Magenta ink number | Sensitivity (mJ/cm$^2$) (mJ/cm$^2$) | Flexibility | Adhesiveness |
|---|---|---|---|---|
| Example 1 | 1 | 165 | 5 | 5B |
| Example 8 | 10 | 20 | 4 | 5B |
| Comparative example 3 | 11 | 450 | 3 | 1B |

As evident from Table 2, even when an ultraviolet emitting diode was used as the radiation source, the ink composition according to the invention (magenta ink 10) was more highly sensitively cured, and formed an image having excellent flexibility and adhesiveness to the substrate (recording medium) in comparison with Comparative Example 3. The comparison between Example 1 using an ultraviolet lamp and Example 8 using an ultraviolet emitting diode, which are shown in Tables 1 and 2, respectively, indicates that higher curing sensitivity was achieved by irradiation with a radiation ray emitted from an ultraviolet emitting diode.

Example 9

Preparation of Support

Molten aluminum was prepared by using an aluminum alloy in a composition (consisting of Al, Si: 0.06 mass %, Fe: 0.30 mass %, Cu: 0.025 mass %, Mn: 0.001 mass %, Mg: 0.001 mass %, Zn: 0.001 mass %, Ti: 0.03 mass %, and unavoidable impurities); and the molten aluminum was filtered and molded into ingots having a thickness of 500 mm and a width of 1,200 mm by DC casting. The surface of the ingot was scraped to an average depth of 10 mm by a surface grinder, and the ingot was heated consistently at 550° C. for approximately 5 hours, and hot-rolled into a rolled plate having a thickness of 2.7 mm after it is cooled to a temperature of 400° C. The plate was heat-treated additionally at 500° C. in a continuous annealing machine, and cold-rolled into a JIS1050 aluminum plate having a thickness of 0.24 mm. The width and the length of the average crystal grain in the aluminum plate obtained were respectively 50 μm and 300 μm. After the aluminum plate was cut to a width of 1,030 mm, it was subjected to the following surface treatment.

<Surface Treatment>

The following various treatments (a) to (j) were performed sequentially. The processing solution remaining on the aluminum plate was removed by nip rollers after each treatment and after washing with water.

(a) Mechanical Surface-Roughening Treatment

The aluminum plate was subjected to mechanical surface-roughening treatment using rotating nylon brush rollers while a suspension, as an abrasive slurry, of an abrasive material (pumice) having a specific gravity of 1.12 in water was being supplied to the aluminum plate surface. The abrasive material had an average particle size of 30 μm, and a maximum size of 100 μm. The nylon brushes were made of nylon 6/10 and had a bristle length of 45 mm and a bristle diameter of 0.3 mm. Three rotating brush rollers were used, each of which being composed of a perforated stainless-steel cylinder having a diameter of 300 mm and bundles of such nylon bristles densely attached thereto by filling them into the perforations. The apparatus had under the brush rollers two supporting rollers (200 mm in diameter), separated from each other at a distance of 300 mm. The brush rollers were pressed against the aluminum plate in such a degree that the load imposed on the driving motor rotating the brush rollers increased to a value higher by 7 kW than that as measured before the brush rollers were pressed against the aluminum plate. The direction of rotation of the brush rollers was the same as the direction of running of the aluminum plate, and the rotational speed thereof was 200 rpm.

(b) Alkali Etching Treatment

The aluminum plate was etched by spraying with an aqueous etching solution, containing 2.6 mass % of caustic soda and 6.5 mass % of aluminum ions with a temperature of 70°

C., to dissolve the aluminum plate in an amount of 10 g/m². Thereafter, the aluminum plate was washed with water by spraying.

(c) Desmutting Treatment

The aluminum plate was desmutted by spraying with an aqueous 1 mass % nitric acid solution (containing 0.5 mass % of aluminum ions) having a temperature of 30° C. Thereafter, the aluminum plate was washed with water by spraying. The aqueous nitric acid solution used for the desmutting treatment was a waste liquid resulting from the process of electrochemical surface-roughening treatment with an alternating current in an aqueous nitric acid solution.

(d) Electrochemical Surface-Roughening Treatment

The aluminum plate was continuously subjected to electrochemical surface roughening using a 60 Hz AC voltage. The electrolytic solution used was an aqueous 10.5 g/L nitric acid solution (also containing 5 g/L of aluminum ions and 0.007 mass % of ammonium ions) having a temperature of 50° C. The AC power source used was one providing a trapezoidal rectangular wave alternating current wherein the time required for the current value to increase from zero to a peak was 0.8 msec and the duty ratio was 1:1. A carbon electrode was used as a counter electrode, and ferrite was used as an auxiliary anode to carry out the electrochemical surface-roughening treatment.

The current density was 30 A/dm² in terms of peak value, and the quantity of electricity was 220 C/dm² in terms of the sum of electricity at the time when the aluminum plate was functioning as an anode. 5% of the current flowing from the power source was supplied to the auxiliary anode. After this surface-roughening treatment, the aluminum plate was washed with water by spraying.

(e) Alkali Etching Treatment

The aluminum plate was etched by spraying with an aqueous solution containing 26 mass % of caustic soda and 6.5 mass % of aluminum ions at a temperature of 32° C. to dissolve the aluminum plate in an amount of 0.50 g/m². Thus, the smut components composed mainly of aluminum hydroxide produced by the preceding step of electrochemical surface-roughening treatment with an alternating current were removed and, simultaneously therewith, the edges of the pits formed were partly dissolved away and rounded to be smooth. Thereafter, the aluminum plate was washed with water by spraying.

(f) Desmutting Treatment

The aluminum plate was desmutted by spraying with an aqueous 15 mass % nitric acid solution (containing 4.5 mass % of aluminum ions) having a temperature of 30° C. Thereafter, the aluminum plate was washed with water by spraying. The aqueous nitric acid solution used for the desmutting treatment was a waste liquid resulting from the step of electrochemical surface-roughening treatment with an alternating current in an aqueous nitric acid solution.

(g) Electrochemical Surface Roughening Treatment

The aluminum plate was continuously subjected to electrochemical surface roughening using a 60 Hz AC voltage. The electrolytic solution used was an aqueous 5.0 g/L hydrochloric acid solution (containing 5 g/L of aluminum ions) having a temperature of 35° C. The AC power source used was one providing a trapezoidal rectangular wave alternating current wherein the time required for the current value to increase from zero to a peak was 0.8 msec and the duty ratio was 1:1. A carbon electrode was used as a counter electrode, and ferrite was used as an auxiliary anode to carry out the electrochemical surface-roughening treatment.

The current density was 25 A/dm² in terms of peak value, and the quantity of electricity was 50 C/dm² in terms of the sum of electricity at the time when the aluminum plate was functioning as an anode. After this surface-roughening treatment, the aluminum plate was washed with water by spraying.

(h) Alkali Etching Treatment

The aluminum plate was etched by spraying with an aqueous solution containing 26 mass % of caustic soda and 6.5 mass % of aluminum ions at a temperature of 32° C. to dissolve the aluminum plate in an amount of 0.12 g/m². Thus, the smut components composed mainly of aluminum hydroxide produced by the preceding step of electrochemical surface-roughening treatment with an alternating current were removed and, simultaneously therewith, the edges of the pits formed were partly dissolved away and rounded to be smooth. Thereafter, the aluminum plate was washed with water by spraying.

(i) Desmutting Treatment

The aluminum plate was desmutted by spraying with an aqueous 25 mass % nitric acid solution (containing 0.5 mass % of aluminum ions) having a temperature of 60° C. Thereafter, the aluminum plate was washed with water by spraying.

(j) Anodizing Treatment

An anodizing apparatus (lengths of first and second electrolysis zones, 6 m each; lengths of first and second feed zones, 3 m each; lengths of first and second feed zones, 2.4 m each) was used to anodize the aluminum plate. Sulfuric acid was used as the electrolytic solution supplied to the first and second electrolysis zones. Each of the electrolytic solution had 50 g/L of sulfuric acid (containing 0.5 mass % of aluminum ions) and a temperature of 20° C. Thereafter, the aluminum plate was washed with water by spraying. The final amount of the oxidized film was 2.7 g/m².

(Preparation and Evaluation of Planographic Printing Plates)

An image was formed and cured in the same manner as Example 1 on the aluminum support prepared above using the ink composition (magenta) of Example 1.

Using this as a planographic printing plate, the image formed and printing durability were evaluated by the following methods.

(a. Image Evaluation)

The planographic printing plate prepared using the ink composition of Example 1 was set in a Heidelberg KOR-D printer, and printing was carried out while an ink [VALUES-G Red for sheet-fed press (manufactured by Dainippon Ink And Chemicals, Incorporated)] and dampening water [trade name: ECOLITY 2, manufactured by Fuji Film Co., Ltd.]] were supplied. The printed material after printing 100 sheets was evaluated by visual observation. From the results, it was confirmed that the image was favorable with no white spots in the image areas and no stain in the non-image areas.

(b. Printing Durability)

Printing was continued to give 10,000 or more sheets of high-quality printed materials with no white spots in the image areas and no stain in the non-image areas, which indicates that practically acceptable printing durability was provided.

Exemplary embodiments of the present invention are described below.

1. An ink composition including a compound that is represented by the following formula (I) and that contains a single oxirane fragment, as a partial structure in at least one bicyclic or tricyclic one,

What is claimed is:

1. An ink composition comprising a monofunctional compound that is represented by the following formula (I) and that contains a single oxirane fragment, as a partial structure in at least one bicyclic or tricyclic ring,

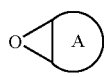

Formula (I)

wherein, in the formula (I), A represents a group of atoms forming a bicyclic or a tricyclic ring, and wherein the content of the monofunctional compound is from 0.5 mass % to 20 mass % with respect to the total solids content constituting the ink composition.

2. The ink composition of claim 1 which further comprises at least one compound that is an epoxy compound, a vinyl ether compound, or another oxetane compound that is not included in the formula (I).

3. The ink composition of claim 1 which further comprises a compound which generates an acid by irradiation with radiation.

4. The ink composition of claim 1 which further comprises a coloring agent.

5. The ink composition of claim 4 wherein the coloring agent is a pigment or an oil soluble dye.

6. The ink composition of claim 5 wherein the oxidation potential of the oil soluble dye is 1.0 V (vs SCE) or more.

7. The ink composition of claim 1 which further comprises at least an oxetane compound that is not included in the formula (I).

8. The ink composition of claim 1 wherein a substituent of at least one bicyclic or tricyclic ring in the formula (I) is selected from the group consisting of an alkyl group, an alkenyl group, an alkynyl group, an aryl group, an aralkyl group, a hydrogen atom, a halogen atom, a hydroxyl group, and a mercapto group.

9. The ink composition of claim 8 wherein the substituent is an alkyl group.

10. An inkjet recording composition comprising the ink composition of claim 1.

11. An inkjet recording method comprising: ejecting the ink composition of claim 1 onto a recording medium using an inkjet recording apparatus; and curing the ink composition by irradiating the ejected ink composition with actinic radiation.

12. The inkjet recording method of claim 11 wherein the actinic radiation is ultraviolet light emitted from a light emitting diode that emits ultraviolet light having a emission peak wavelength within the range of 350 to 420 nm and achieves a maximum illumination intensity of 10 to 2,000 mW/cm$^2$ at the surface of the recording medium.

13. Printed material that has been recorded by the inkjet recording method of claim 11.

14. A method for producing a planographic printing plate, the method comprising ejecting the ink composition of claim 1 onto a support, and forming a hydrophobic image on the support by irradiating the ejected ink composition with actinic radiation to cure the ink composition.

15. A planographic printing plate that has been produced by the method for producing a planographic printing plate of claim 14.

* * * * *